(12) United States Patent
Ueda

(10) Patent No.: US 8,802,706 B2
(45) Date of Patent: Aug. 12, 2014

(54) METHOD FOR TREATING FIBROMYALGIA

(75) Inventor: Hiroshi Ueda, Nagasaki (JP)

(73) Assignees: Nagasaki University, Nagasaki (JP); Kabushiki Kaisha M.S.S, Tokyo (JP)

( * ) Notice: Subject to any disclaimer, the term of this patent is extended or adjusted under 35 U.S.C. 154(b) by 332 days.

(21) Appl. No.: 13/057,888

(22) PCT Filed: Aug. 7, 2009

(86) PCT No.: PCT/JP2009/064062
§ 371 (c)(1),
(2), (4) Date: Mar. 24, 2011

(87) PCT Pub. No.: WO2010/016590
PCT Pub. Date: Feb. 11, 2010

(65) Prior Publication Data
US 2011/0182917 A1    Jul. 28, 2011

(30) Foreign Application Priority Data

Aug. 7, 2008 (JP) .................. 2008-204762
May 7, 2009 (JP) .................. 2009-112990

(51) Int. Cl.
*A61K 31/44* (2006.01)
*A61K 31/42* (2006.01)
*C07D 401/00* (2006.01)
*C07D 261/14* (2006.01)
*A61P 25/00* (2006.01)

(52) U.S. Cl.
USPC ......... 514/380; 514/340; 546/268.1; 548/244

(58) Field of Classification Search
None
See application file for complete search history.

(56) References Cited

FOREIGN PATENT DOCUMENTS

| | | |
|---|---|---|
| JP | 2004-506604 A | 3/2004 |
| WO | WO 01/71022 A2 | 9/2001 |
| WO | WO 2009/064497 A1 | 5/2009 |
| WO | WO 2010/077883 A2 | 7/2010 |

OTHER PUBLICATIONS

Gardell et al., *Trends in Molecular Medicine*, 12(2): 65-75 (2006).
Inoue et al., *Nature Medicine*, 10(7): 712-718 (2004).
Inoue et al., *Neuroscience*, 152: 296-298 (2008).
Inoue et al., *Molecular Pain*, 4(6): 1-5 (2008) [doi: 10.1186/1744-8069-4-6].
Murata et al., *The Journal of Biological Chemistry*, 269(48): 30479-30484 (1994).
Ueda, Hiroshi, *Pharmacology & Therapeutics*, 109: 57-77 (2006).
Ueda, Hiroshi, *Pharma Medica*, 24(6): 15-19 (2006).
Japanese Patent Office, International Search Report in International Application No. PCT/JP2009/064062 (Sep. 15, 2009).
Japanese Patent Office, International Preliminary Report on Patentability in International Application No. PCT/JP2009/064062 (Mar. 8, 2011).
Xie et al., *Molecular Pain, Biomed. Central*, London, GB, 4(1): p. 46 (2008).
European Patent Office, Supplemental European Search Report in European Patent Application No. 09805072.7 (Oct. 16, 2012).
Gierse et al., *J. Pharmacol. Exp. Ther.*, 334(1): 310-317 (2010).
Kawaguchi et al., *ACS Chemical Biology*, 8: 1713-1721 (2013).
Ohta et al., *Molecular Pharmacology*, 64(4): 994-1005 (2003).
Zhao et al., *Molecular Pharmacology*, 73(2): 587-600 (2008).

*Primary Examiner* — Christine J Saoud
*Assistant Examiner* — Jon M Lockard
(74) *Attorney, Agent, or Firm* — Leydig, Voit & Mayer, Ltd.

(57) ABSTRACT

Provided is a therapeutic or prophylactic agent for generalized pain syndrome, for which no cause and therapies have been established. A therapeutic or prophylactic agent for generalized pain syndrome containing an LPA1 antagonist or autotaxin-inhibiting substance as an active ingredient. The pharmaceutical is preferably administered to the central nervous system. The generalized pain syndrome is preferably fibromyalgia, chronic fatigue syndrome or hypersensitivity colitis.

1 Claim, 5 Drawing Sheets

METHOD FOR TREATING FIBROMYALGIA

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 66,533 bytes ASCII (Text) file named "707646SequenceListing.txt," created Feb. 7, 2011.

TECHNICAL FIELD

The present invention relates to a therapeutic or prophylactic agent for generalized pain syndrome. Specifically, the present invention relates to the field of pharmaceuticals that help treat chronic pains.

BACKGROUND ART

There are two types of pains: acutely occurring pains as a self-warning to living organisms and chronically developing pains as an illness. While there is a demand for recovery from chronic pains by treatments, including drugs, a nonnegligible number of patients suffer intractable diseases for which no therapies have been established because the causal mechanism of onset remains unclear. Among them is generalized pain syndrome. Generalized pain syndrome is a disease of unknown cause that produces intense pain over a wide area of the body, and it is difficult to detect ecologically abnormal findings by examinations. Because generalized pain syndrome tends to often become chronic, it is positioned as an intractable chronic pain. Not only patients experience disturbances in their daily activities and labor, but also there are not a few cases wherein they have mental concerns, including the inability to determine which department to visit, the lack of an established diagnosis, even by extensive examinations, due to the low availability of specialist physicians, the absence of therapeutic drugs, being deemed idle, and the like. In fact, it is known that in addition to pains, generalized pain syndrome is often complicated by a sensation of fatigue, depression, anxiety and the like. Additionally, fibromyalgia, a form of generalized pain syndrome, occurs most prevalently among middle-aged to elderly women, and it has been found that physical traumas from surgery or accidents and stress-related mental factors are profoundly involved in the background of the onset.

Lysophosphatidic acid (LPA) is a lipid mediator produced at the time of tissue damage, known to act on 7-pass transmembrane receptors (LPA1, LPA2, LPA3) that couple with various G proteins ($G_{q/11/14}$, $G_{12/13}$, $G_{i/o}$) to serve as a trophic factor for various cells, including nerve and glial cells.

The present inventor, through many years of research into the molecular mechanisms behind neuropathic pains, revealed that LPA is a substance that induces neuropathic pains, and reported that nerve injury-induced pain does not develop when a receptor of LPA is lacked using knockout mice prepared by knock out of LPA1, a kind of LPA receptor (Non-patent Documents 1 and 2).

The present inventor demonstrated that LPA is synthesized from lysophosphatidylcholine (LPC), which is a constituent of the cell membrane, by the LPA synthetase autotaxin (ATX), and is involved in irritation development (Non-patent Documents 3 and 4).

PRIOR ART DOCUMENTS

Non-patent Documents

Non-patent Document 1: Inoue M, et al Nat Med 10: p. 712-718, 2004
Non-patent Document 2: Ueda H Pharmacol Ther 109: p. 57-77, 2006
Non-patent Document 3: Inoue M, et al Neuroscience 152: p. 296-298, 2008
Non-patent Document 4: Inoue M, et al Molecular Pain, 4: 6, 2008

SUMMARY OF THE INVENTION

Problems to be Solved by the Invention

It is an object of the present invention to provide a therapeutic or prophylactic agent for generalized pain syndrome, for which no cause and therapies have been established.

Means of Solving the Problems

Taking note of stress as a cause of induction of generalized pain syndrome, the present inventor attempted to clarify the cause of generalized pain disease using animal models actually exposed to stress. The present inventor conducted further extensive investigations, found that LPA is profoundly involved not only in the peripheral nervous system, but also in the central nervous system in individuals affected by generalized pain syndrome, and has developed the present invention. Accordingly, the invention of this application is as follows:

[1] A therapeutic or prophylactic agent for generalized pain syndrome comprising an LPA1 antagonist as an active ingredient.
[2] The therapeutic or prophylactic agent described in [1] above, wherein the LPA1 antagonist is selected from the group consisting of antisense nucleic acids, siRNAs and antagonist antibodies against LPA1, soluble LPA1 and low-molecular compounds that bind to LPA1 to inhibit signaling.
[3] The therapeutic or prophylactic agent described in [1] or [2] above, wherein the LPA1 antagonist is administered to the central nervous system.
[4] The therapeutic or prophylactic agent described in any one of [1] to [3] above, wherein the generalized pain syndrome is fibromyalgia, chronic fatigue syndrome or hypersensitivity colitis.
[5] A therapeutic or prophylactic agent for generalized pain syndrome comprising an autotaxin-inhibiting substance as an active ingredient.
[6] The therapeutic or prophylactic agent described in [5] above, wherein the autotaxin-inhibiting substance is selected from the group consisting of antisense nucleic acids, siRNAs and inhibitory antibodies against autotaxin and low-molecular compounds that inhibit the enzyme activity of autotaxin.
[7] The therapeutic or prophylactic agent described in [5] or [6] above, wherein the autotaxin-inhibiting substance is administered to the central nervous system.
[8] The therapeutic or prophylactic agent described in any one of [5] to [7] above, wherein the generalized pain syndrome is fibromyalgia, chronic fatigue syndrome or hypersensitivity colitis.
[9] A method of treating or preventing generalized pain syndrome comprising a step for administering an effective amount of an LPA1 antagonist to a subject in need thereof.

[10] The therapeutic or prophylactic method described in [9] above, wherein the LPA1 antagonist is selected from the group consisting of antisense nucleic acids, siRNAs and antagonist antibodies against LPA1, soluble LPA1 and low-molecular compounds that bind to LPA1 to inhibit signaling.
[11] The therapeutic or prophylactic method described in [9] or [10] above, wherein the LPA1 antagonist is administered to the central nervous system.
[12] The therapeutic or prophylactic method described in any one of [9] to [11] above, wherein the generalized pain syndrome is fibromyalgia, chronic fatigue syndrome or hypersensitivity colitis.
[13] A method of treating or preventing generalized pain syndrome comprising a step for administering an effective amount of an autotaxin-inhibiting substance to a subject in need thereof.
[14] The therapeutic or prophylactic method described in [13] above, wherein the autotaxin-inhibiting substance is selected from the group consisting of antisense nucleic acids, siRNAs and inhibitory antibodies against autotaxin and low-molecular compounds that inhibit the enzyme activity of autotaxin.
[15] The therapeutic or prophylactic method described in [13] or [14] above, wherein the autotaxin-inhibiting substance is administered to the central nervous system.
[16] The therapeutic or prophylactic method described in any one of [13] to [15] above, wherein the generalized pain syndrome is fibromyalgia, chronic fatigue syndrome or hypersensitivity colitis.
[17] A use of an LPA1 antagonist for producing the therapeutic or prophylactic agent for generalized pain syndrome described in any one of [1] to [4] above.
[18] A use of an autotaxin-inhibiting substance for producing the therapeutic or prophylactic agent for generalized pain syndrome described in any one of [5] to [8] above.

Effect of the Invention

According to a therapeutic or prophylactic agent for generalized pain disease of the present invention, it is possible to make a major contribution to the establishment of an effective and reliable therapeutic policy and prophylactic method for generalized pain disease, for which no therapies have been established to date because the cause remains unclear.

MODE FOR EMBODYING THE INVENTION

Figure 1:
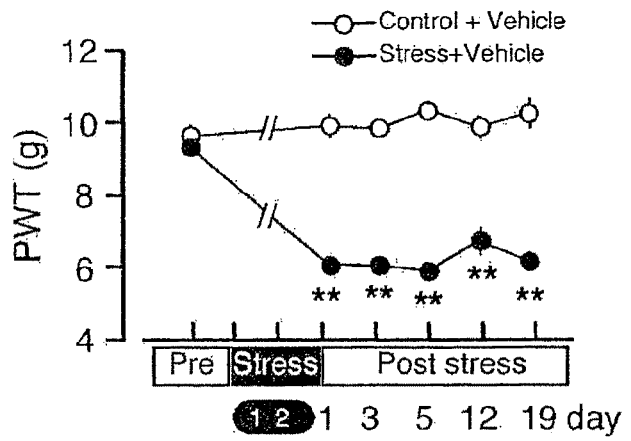
FIG. 1 is a graphic representation showing results of the mechanical stimulus-induced pain test of Example 3 performed on Vehicle-treated mice.

A therapeutic or prophylactic agent of the present invention comprises an LPA1 antagonist as an active ingredient.

In the present invention, LPA1 (lysophosphatidic acid receptor 1) refers to a kind of 7-pass transmembrane receptor, a ligand thereto being LPA (lysophosphatidic acid), which couples with G protein, and is also referred to as EDG2 (endothelial differentiation lysophosphatidic acid G protein coupled receptor 2). While LPA1, LPA2 and LPA3 have been identified as lysophosphatidic acid receptors so far, LPA1 is targeted in relation to the diseases to which the present invention is directed. The gene that encodes LPA1 may have a base sequence derived from any animal. For example, for developing a therapeutic drug for humans, the human LPA1 gene is preferred. When using mice, which are readily utilizable laboratory animals, the analytical results from the mice are well expected to reflect pathologic conditions in other mammals, including humans; therefore, it is also preferable to use the mouse LPA1 gene. Herein, the human LPA1 gene is based on the base sequence disclosed in Genbank Accession No. NM_001401 (SEQ ID NO:1). The mouse LPA1 gene is based on the base sequence disclosed in Genbank Accession No. NM_010336 (SEQ ID NO:3). LPA1 homologues derived from other animals can be identified using Homolo-Gene (www.ncbi.nlm.nih.gov/HomoloGene/). Specifically, a particular human base sequence is applied to BLAST (Proc. Natl. Acad. Sci. USA 90:5873-5877, 1993, www.ncbi.nlm.nih.gov/BLAST/), and the accession number of the identical (exhibiting the highest Score, an E-value of 0 and 100% Identity) sequence is acquired. The accession number is input to UniGene (www.ncbi.nlm.nih.gov/UniGene/), and the thus-obtained UniGene Cluster ID (a number shown by Hs.) is input to HomoloGene. From the resulting list of gene homologue correlations between the genes of other biological species and the human gene, genes of other biological species can be selected as genes corresponding to the human gene shown by the particular base sequence (homologues).

Likewise, in the present invention, the human LPA1 protein is based on the amino acid sequence disclosed in Genbank Accession No. NM_001401 (SEQ ID NO:2). The mouse LPA1 protein is based on the amino acid sequence disclosed in Genbank Accession No. NM_010336 (SEQ ID NO:4).

In the present invention, an LPA1 antagonist generically refers to substances acting to antagonize the receptor LPA1, possessing the action reverse to that of LPA, which is a natural agonist of LPA1. LPA1 antagonists include not only substances that bind to LPA1 to inhibit the signaling from the receptor, but also substances that inhibit the binding of LPA1 and LPA, for example, substances that capture LPA (for example, soluble LPA1, which captures LPA in the blood, and the like) and the like. Furthermore, LPA1 antagonists also include substances that inhibit factors downstream of the signaling from the LPA1 receptor. Such substances include Botulinus toxin C3, which inhibits RhoA activity, Y-27632, which inhibits Rho kinase activity, and the like.

LPA1 antagonists include antagonists that have been shown to possess antagonistic activity to date, or all substances whose antagonistic activity can be confirmed using the model of stress-induced generalized pain described below. Specifically, ones selected from the group consisting of an antisense nucleic acid, siRNA, viral vector-recombined shRNA, microRNA and antagonist antibody against LPA1, soluble LPA1 and a low-molecular compound that binds to LPA1 to inhibit signaling can be mentioned as examples. These may be natural substances or artificially synthesized substances.

The aforementioned antisense nucleic acid against LPA1 refers to, for example, a single-stranded nucleic acid complementary to at least a part of base sequence selected from among the base sequence of SEQ ID NO:1 or 3 or the base sequence that encodes the amino acid sequence of SEQ ID NO:2 or 4. The nucleic acid may be a naturally derived or artificial nucleic acid, or may be one based on DNA or RNA. The length of the antisense nucleic acid is normally about 15 bases to the same as the full length of the mRNA, preferably about 15 to about 30 bases long. The complementarity of the antisense nucleic acid does not always need to be 100%, and may be of a degree that allows complementary binding to the DNA or RNA of LPA1 in a living organism.

The aforementioned siRNA refers to a double-stranded RNA synthesized artificially to cause the degradation of the mRNA transcribed from the LPA1 gene (RNA interference) on the basis of the base sequence thereof, or a vector capable of supplying the double-stranded RNA in a living organism, in order to suppress the expression of the LPA1 gene. Using the siRNA or siRNA expression vector of the present invention, it is possible to have an action to suppress generalized pains by reducing the expression of LPA1 to inhibit the signaling from LPA1. To construct an siRNA or siRNA expression vector, a publicly known method can be used (Ui-Tei K, et al., Nucleic Acids Res. 2004; 32: 936-948; Miyagishi M, and Taira K, Nature biotechnology 2002; 20: 497-500). The length of the siRNA is preferably 19 to 27 bp, more preferably 21 to 25 bp. In the shRNA and microRNA, a partial gene of the LPA1 gene is recombined into an appropriate viral vector and administered as a virus systemically or to the brain or the spinal cord, whereby the LPA1 gene is knocked down. The length of the partial gene is preferably 60 to 70 bp in each case.

The aforementioned antagonist antibody against LPA1 refers to an antibody that binds specifically to LPA1 and inhibits the signaling from LPA1 by binding thereto. This antagonist antibody is preferably an antibody that recognizes an extracellular domain of LPA1 and the like.

As mentioned herein, "antibodies" include natural type antibodies such as polyclonal antibodies and monoclonal antibodies, chimeric antibodies, humanized antibodies and single-stranded antibodies produced using gene recombination technology, human antibodies that can be produced using human antibody-producing transgenic animals and the like, antibodies prepared by phage display and binding fragments thereof.

A binding fragment means a partial region of one of the above-described antibodies; specifically, for example, F(ab')$_2$, Fab', Fab, Fv (variable fragment of antibody), sFv, dsFv (disulphide stabilized Fv), dAb (single domain antibody) and the like can be mentioned (Exp. Opin. Ther. Patents, Vol. 6, No. 5, p. 441-456, 1996).

The class of antibody is not particularly limited; antibodies of any isotypes such as IgG, IgM, IgA, IgD and IgE are encompassed. Preferably, the class is IgG or IgM, and in view of the ease of purification and the like, IgG is more preferable.

A polyclonal antibody or a monoclonal antibody can be produced by a known ordinary method of production. Specifically, for example, an immunogen, along with Freund's Adjuvant as required, is given for immunization to a mammal, for example, a mouse, rat, hamster, guinea pig, rabbit, cat, dog, pig, goat, horse or bovine, preferably a mouse, rat, hamster, guinea pig, goat, horse or rabbit, in the case of a polyclonal antibody, or to a mouse, rat or hamster in the case of a monoclonal antibody.

Specifically, a polyclonal antibody can be produced as described below. An immunogen is injected to a mouse, rat, hamster, guinea pig, goat, horse or rabbit, preferably to a goat, horse or rabbit, more preferably to a rabbit, subcutaneously, intramuscularly, intravenously, into a footpad or intraperitoneally, once to several times, whereby the animal is immunologically sensitized. Normally, 1 to 5 immunizations are performed at intervals of about 1 to 14 days from initial immunization, and about 1 to 5 days after final immunization, a serum is acquired from the immunologically sensitized mammal.

Although the serum can be used as a polyclonal antibody, it is preferably isolated and/or purified by ultrafiltration, ammonium sulfate fractionation, the euglobulin precipitation method, the caproic acid method, the caprylic acid method, ion exchange chromatography (DEAE or DE52 and the like), or affinity column chromatography using an anti-immunoglobulin column, a protein A/G column, an immunogen-crosslinked column or the like.

A monoclonal antibody is produced by preparing a hybridoma from a cell that produces the antibody, obtained from the above-described immunologically sensitized animal, and a myeloma-series cell (myeloma cell) not having the capability of autoantibody production, cloning the hybridoma, and selecting a clone that produces a monoclonal antibody that exhibits specific affinity for the immunogen used to immunize the mammal.

Specifically, a monoclonal antibody can be produced as described below. An immunogen is injected once to several times, or transplanted, to a mouse, rat or hamster (including transgenic animals created to produce an antibody derived from another animal, like human antibody-producing transgenic mice) subcutaneously, intramuscularly, intravenously, into a footpad or intraperitoneally, whereby the animal is immunologically sensitized. Normally, 1 to 4 immunizations are performed at intervals of about 1 to 14 days from initial immunization, and about 1 to 5 days after final immunization, antibody-producing cells are acquired from the immunologically sensitized the mammal.

Preparation of a Hybridoma (Fusion Cell) that Secretes a monoclonal antibody can be performed according to the method of Kohler and Milstein et al. (Nature, Vol. 256, p. 495-497, 1975) or a modified method based thereon. Specifically, the hybridoma is prepared by cell-fusion of an antibody-producing cell contained in a spleen, lymph node, bone marrow, tonsil or the like, preferably in a spleen, acquired from a mammal immunologically sensitized as described above, and a myeloma cell not having the capability of autoantibody production, preferably derived from a mammal such as a mouse, rat, guinea pig, hamster, rabbit or human, more preferably from a mouse, rat or human.

Examples of useful myeloma cells for the cell fusion include the mouse-derived myeloma P3/X63-AG8.653 (653; ATCC No. CRL1580), P3/NSI/1-Ag4-1 (NS-1), P3/X63-Ag8.U1 (P3U1), SP2/0-Ag14 (Sp2/0, Sp2), PAI, F0 or BW5147, the rat-derived myeloma 210RCY3-Ag.2.3., and the human-derived myeloma U-266AR1, GM1500-6TG-A1-2, UC729-6, CEM-AGR, D1R11 or CEM-T15.

Screening for a hybridoma clone that produces a monoclonal antibody can be performed by culturing a hybridoma in, for example, a microtiter plate, and measuring the reactivity of the culture supernatant of proliferative hybridoma in a well to the immunogen used in the immunological sensitization, by, for example, an enzyme immunoassay such as ELISA.

The hybridoma may be cultured using a medium (for example, DMEM containing 10% fetal bovine serum), and a centrifugal supernatant of the culture broth may be used as a monoclonal antibody solution. It is also possible to inject this hybridoma into the abdominal cavity of the animal from which it is derived to thereby produce ascites fluid, and to use the thus-obtained ascites fluid as a monoclonal antibody solution. The monoclonal antibody, like the above-described polyclonal antibody, is preferably isolated and/or purified.

A chimeric antibody can be produced with reference to, for example, "Jikken Igaku (extra issue), Vol. 6, No. 10, 1988", JP-B-HEI-3-73280 and the like; a humanized antibody can be prepared with reference to, for example, JP-T-HEI-4-506458, JP-A-SHO-62-296890 and the like; a human antibody can be prepared with reference to, for example, "Nature Genetics, Vol. 15, p. 146-156, 1997", "Nature Genetics, Vol. 7, p. 13-21, 1994", JP-T-HEI-4-504365, International Patent Application Publication WO94/25585, "Nikkei Science, June issue, pages 40 to 50, 1995", "Nature, Vol. 368, p. 856-859, 1994", JP-T-HEI-6-500233) and the like.

In preparing an antibody by phage display, an antibody such as Fab can easily be obtained from a phage library prepared for antibody screening, by, for example, recovering and concentrating a phage with affinity for the antigen by biopanning. For the preparation of an antibody by phage display, see "Nature, Vol. 348, p. 552-554, 1990", "Phage display a laboratory manual" In cold spring harbor laboratory press, 2001", and "Antibody Engineering—a Practical Approach, IRL Press, Oxford, 1996".

F(ab')$_2$ and Fab' can be produced by treating an immunoglobulin with the proteinase pepsin or papain, respectively. Fab can be produced by screening a Fab expression phage library in the same manner as the above-described method of antibody preparation by phage display.

The aforementioned soluble LPA1 is a decoy receptor that binds to LPA but does not allow the signaling into cells to occur. Soluble LPA1 has the function of suppressing the signaling from LPA1 mainly by trapping LPA in the blood to reduce the amount of LPA bound to LPA1. As such, soluble LPA1 can be prepared by a publicly known gene engineering technique on the basis of the amino acid sequence that constitutes an extracellular domain of the receptor.

The aforementioned low-molecular compound is exemplified by the compounds disclosed in WO2002/062389, WO2003/007991, WO2003/024402 (JP-T-2005-508319) or WO2005/032494 (JP-T-2007-508324) and the like. As commercially available antagonists, ammonium (S)-mono-{2-octadeca-9-enoylamino-3-[4-(pyridin-2-ylmethoxy)-phenyl]-propyl}phosphate, ammonium (S)-mono-[3(4-benzyloxy-phenyl)-2-octadeca-9-enoylamino-propyl]phosphate, and the like can be mentioned.

A therapeutic or prophylactic agent of the present invention comprises an autotaxin-inhibiting substance as an active ingredient.

In the present invention, autotaxin (ATX) is also referred to as ENPP (ectonucleotide pyrophosphatase/phosphodiesterase) 2; it is an enzyme that catalyzes the synthesis of LPA from lysophosphatidylcholine (LPC), which is a constituent of the cell membrane, possessing lysophospholipase D (LPLD) activity. The gene that encodes ATX may have a base sequence derived from any animal. For example, for developing a therapeutic drug for humans, the human ATX gene is preferred. When using mice, which are readily utilizable laboratory animals, the analytical results from the mice are well expected to reflect pathologic conditions in other mammals, including humans; therefore, it is also preferable to use the mouse ATX gene. Herein, the human ATX gene is based on the base sequence disclosed in Genbank Accession No. NM_006209 (SEQ ID NO:9). The mouse ATX gene is based on the base sequence disclosed in Genbank Accession No. NM_015744 (SEQ ID NO:11). ATX homologues derived from other animals can be identified using HomoloGene (www.ncbi.nlm.nih.gov/HomoloGene/). Specifically, a particular human base sequence is applied to BLAST (Proc. Natl. Acad. Sci. USA 90:5873-5877, 1993, www.ncbi.nlm.nih.gov/BLAST/), and the accession number of the identical (exhibiting the highest Score, an E-value of 0 and 100% Identity) sequence is acquired. The accession number is input to UniGene (www.ncbi.nlm.nih.gov/UniGene/), and the thus-obtained UniGene Cluster ID (a number shown by Hs.) is input to HomoloGene. From the resulting list of gene homologue correlations between the genes of other biological species and the human gene, genes of other biological species can be selected as genes corresponding to the human gene shown by the particular base sequence (homologues).

Likewise, in the present invention, the human ATX protein is based on the amino acid sequence disclosed in Genbank Accession No. NM_006209 (SEQ ID NO:10). The mouse ATX protein is based on the amino acid sequence disclosed in Genbank Accession No. NM_015744 (SEQ ID NO:12).

In the present invention, an ATX inhibiting substance generically refers to substances that inhibit the expression of ATX and substances that inhibit the enzyme activity of ATX. Substances that inhibit the enzyme activity of ATX include not only substances that interact with ATX to inhibit the enzyme activity thereof, but also substances that inhibit the binding of ATX and LPA and the like. A substance that inhibits the expression of ATX can be selected by measuring the expression level of the mRNA or protein of ATX in ATX-expressing cells, and confirming a significant reduction in the expression level compared with a control not containing the substance. A substance that inhibits the enzyme activity of ATX can be selected by adding the substance to a system containing ATX and a substrate therefor (a labeled substrate, for example, fluorescently labeled FS-3 (Echelon Biosciences Company)), and confirming a significant reduction in the amount of the marker leaving the substrate compared with a control not containing the substance.

ATX inhibiting substances include inhibitory substances that have been shown to possess inhibitory activity to date, or all substances whose inhibitory activity can be confirmed using the model of stress-induced generalized pain described below. Specifically, ones selected from the group consisting of an antisense nucleic acid, siRNA, viral vector-recombined shRNA, microRNA and inhibitory antibody against ATX and a low-molecular compound that inhibits the enzyme activity of ATX can be mentioned as examples. These may be natural substances or artificially synthesized substances.

The aforementioned ATX antisense nucleic acid refers to, for example, a single-stranded nucleic acid complementary to at least a part of base sequence selected from among the base sequence of SEQ ID NO:9 or 11 or the base sequence that encodes the amino acid sequence of SEQ ID NO:10 or 12. The nucleic acid may be a naturally derived or artificial nucleic acid, or may be one based on DNA or RNA. The length of the antisense nucleic acid is normally about 15 bases to the same as the full length of the mRNA, preferably about 15 to about 30 bases long. The complementarity of the antisense nucleic acid does not always need to be 100%, and may be of a degree that allows complementary binding to the DNA or RNA of ATX in a living organism.

The aforementioned siRNA refers to a double-stranded RNA synthesized artificially to cause the degradation of the mRNA transcribed from the ATX gene (RNA interference) on the basis of the base sequence thereof, or a vector capable of supplying the double-stranded RNA in a living organism, in order to suppress the expression of the ATX gene. Using the siRNA or siRNA expression vector of the present invention, it is possible to have an action to suppress generalized pains by reducing the expression of ATX to inhibit the production of LPA by ATX. To construct an siRNA or siRNA expression vector, a publicly known method can be used (Ui-Tei K, et al., Nucleic Acids Res. 2004; 32: 936-948; Miyagishi M, and Taira K, Nature biotechnology 2002; 20: 497-500). The length of the siRNA is preferably 19 to 27 bp, more preferably 21 to 25 bp. In the shRNA and microRNA, a partial gene of the ATX gene is recombined into an appropriate viral vector and administered as a virus systemically or to the brain or the spinal cord, whereby the ATX gene is knocked down. The length of the partial gene is preferably 60 to 70 bp in each case.

The aforementioned inhibitory antibody against ATX refers to an antibody that binds specifically to ATX and inhibits the enzyme activity of ATX by binding thereto. Inhibitory antibodies against ATX include the antibodies described in the literature (Nakamura K, et al., Clin Chim Acta. 2008 February; 388 (1-2):51-8. Epub 2007 Oct. 11.) and the like. "Antibody" in an inhibitory antibody against ATX is as explained for the "antibody" in the aforementioned LPA1 antagonist antibody.

As the aforementioned low-molecular compound that inhibits the enzyme activity of ATX, sphingosine 1-phosphatase (S1P), lysophosphatidic acid (LPA), FTY720 (S1P analogue), cyclic PA (natural type analogue of LPA), BrP-LPA (bromomethylenephosphonate LPA), [4-(tetradecanoylamino)benzyl]phosphonic acid (S32826) and the like can be mentioned.

The disease targeted by a therapeutic or prophylactic agent of the present invention is generalized pain syndrome. Generalized pain syndrome generically refers to diseases accompanied by systemic chronic pain for which the cause has not been clarified and no therapies have been established.

Encompassed by the aforementioned generalized pain syndrome are fibromyalgia, chronic fatigue syndrome, hypersensitivity colitis (or temporomandibular disorders) and the like. The onset of these diseases is reportedly profoundly related to a stress. In particular, fibromyalgia, chronic fatigue syndrome, hypersensitivity colitis and the like, which are presumably involved by the action of LPA in the central nervous system, are preferred as targets of treatment by the present invention. In particular, the majority of patients with fibromyalgia have a history of experiencing an injury (e.g., whiplash injury, surgery) in the past, and the involvement of the action of LPA in the hypothalamus is likely. LPA seems to be contributory to the formation and maintenance of pains in the aforementioned diseases.

Therefore, it is preferable that a therapeutic or prophylactic agent of the present invention be administered to the central nervous system for ensuring the effect thereof to be exhibited in full. A method is also available wherein cerebral transfer is promoted by systemic administration in a collagen formulation and the like.

Although any route of administration is acceptable to deliver a therapeutic or prophylactic agent of the present invention to the central nervous system, parenteral administrations are preferred. Parenteral administrations include intravenous injection (drip infusion), subcutaneous administration, intradural administration, intrameningeal administration, spinal epidural administration, spinal subarachnoidal administration, intra-lateral-cerebroventricular administration, intracisternal administration and the like; because of the possible involvement of the upper parts of the brain, intra-lateral-cerebroventricular administration and intracisternal administration are more preferred.

A therapeutic or prophylactic agent of the present invention may contain a pharmaceutically acceptable carrier, depending on the choice and route of administration of the active ingredient LPA1 antagonist or autotaxin-inhibiting substance. Those skilled in the art are able to choose as appropriate a carrier suitable for the situation. Examples of carriers that can be chosen include, but are not limited to, excipients such as sucrose, starch, mannitol, sorbitol, lactose, glucose, cellulose, talc, calcium phosphate, and calcium carbonate; binders such as cellulose, methylcellulose, hydroxypropylcellulose, polypropylpyrrolidone, gelatin, gum arabic, polyethylene glycol, sucrose, and starch; disintegrants such as starch, carboxymethylcellulose, hydroxypropyl starch, sodium-glycol-starch, sodium hydrogen carbonate, calcium phosphate, and calcium citrate; lubricants such as magnesium stearate, Aerosil, talc, and sodium lauryl sulfate; preservatives such as sodium benzoate, sodium hydrogen sulfite, methyl paraben, and propyl paraben; pH regulators such as citric acid, sodium citrate, and acetic acid; suspending agents such as methylcellulose, polyvinylpyrrolidone, and aluminum stearate; dispersing agents such as surfactants; solvents such as water, physiological saline, ethanol, and propylene glycol; isotonizing agents such as glucose, sodium chloride, and potassium chloride; base waxes such as cacao butter, polyethylene glycol, and refined kerosene; and the like. These carriers are not limited to a single action, and can be used for the purpose of having a plurality of actions.

The ratio of the aforementioned active ingredient contained in a therapeutic or prophylactic agent of the present invention can be set as appropriate, as far as the desired effect is obtained; the ratio is normally 0.01 to 100% by weight, preferably 0.1 to 99.9% by weight, more preferably 0.5 to 99.5% by weight.

Although the dosage of a therapeutic or prophylactic agent of the present invention varies depending on the choice of active ingredient, the recipient's body weight and age, symptoms, and the like, and cannot be generalized, it can be chosen over the range from 0.0001 mg to 1000 mg per kg body weight in a single dose.

Recipients of a promotive or prophylactic drug of the present invention include mammals such as mice, rats, hamsters, guinea pigs, rabbits, cats, dogs, bovines, horses, sheep, monkeys, and humans.

Although the dosing frequency of a therapeutic or prophylactic agent of the present invention is not particularly limited, it is normally about 1 to 5 times a day. Since it is highly likely that LPA is contributory to the formation and maintenance of pains in the aforementioned diseases to be treated, preference is given to long-term use for about several days to 1 month. This dosing frequency allows the achievement of preventing the formation and maintenance of pains. Note that in the event of a recurrence of the aforementioned disease after a considerable time interval, the therapeutic or prophylactic agent of the present invention can be administered again.

For the LPA1 antagonist or autotaxin-inhibiting substance that is an active ingredient of a therapeutic or prophylactic agent of the present invention, the effect thereof can be confirmed using an animal model of generalized pain disease created by the method described below. In the animal model described herein, pain threshold value reductions are observed for at least 2 to 3 weeks after completion of repeated stress loading. Pain threshold values are expressed by PWL values (paw withdrawal latency (seconds)) as determined by a mechanical stimulation induction test method (paw pressure test). If the PWL value decreases significantly compared with non-stress-loaded animals as controls, it is judged that the chronic pain persists; if the PWL level rises to the same level as the controls, it is judged that the chronic pain has healed.

Any non-human animal can be used. Suitable animals include laboratory animals such as mice, rats, hamsters, guinea pigs, rabbits, dogs, cats, and monkeys; and farm animals such as bovines, sheep, horses, and pigs; preference given to mice because a wide variety of disease models have been established to date, and also because they permit easy utilization for gene engineering.

Model of Generalized Pain Disease with SART (ICS) Stress

The SART stress model, in which normal temperature and a cold environment are repeatedly loaded, is commonly known as a model of autonomic imbalances of the parasympathetic nerve dominant type; a wide variety of abnormalities, such as persistent hypotension, immune balance abnormalities, and hyperalgesia, have been reported. Meanwhile, the SART stress model is said to be also useful as an animal model of generalized pain syndrome, including fibromyalgia. In the method of creating a model by SART stress, the rearing environment for animals such as mice is repeatedly altered between room temperature (around 24° C.) and cold temperature (around 4° C.); this is desirably referred to as intermittent cold stress (ICS), so as to distinguish it from constant cold stress (CCS stress), which represents conditions only involving cold temperature stress without returning to room temperature as control stress that does not induce chronic pains. As described in Examples, ICS stress is more strictly defined than traditionally reported SART stress. Likewise, how to create a model based on CCS stress is also described in Examples.

EXAMPLES

The present invention is hereinafter described in further detail by means of the following examples, by which, however, the present invention is not limited anyway.

Production Example 1

SART (ICS) Stress Loading Group

Exposure to SART (ICS) stress was achieved by repeatedly altering extremely different rearing environmental temperatures. Temperature settings were established at room temperature (24° C.) and cold temperature (4° C.). Rearing cages were placed in environments set at the respective temperatures; the animals were reared, with transfer of the mice only every 30 minutes in the daytime (from 10:00 to 16:30), and at the cold temperature in the nighttime (from 16:30 to 10:00 on the following day). This repeated stress was given for 3 days from 16:30 on the day before stress loading to 10:00 on day 3 of stress loading. A solid food and agar for water supply were always kept in the cage during the above-described stress loading period, to maintain an environment allowing the animals to have free access thereto.

The mice used for a normal control group were mice reared in the same way as the stress loading group, except that the animals were reared constantly at 24° C. during the above-described stress loading period.

Example 1

A hypersensitive response induction experiment with ICS stress was applied to mice previously dosed with an antisense oligodeoxynucleotide that complementarily binds to the lysophosphatidic acid (hereinafter, denoted as LPA) receptor gene to inhibit the expression thereof (hereinafter, denoted as AS-ODN) as an animal model of generalized pain disease, and the stress exposure of Production Example 1 was performed.

LPA1 AS-ODN-Treated Mice

Ten to twelve C57BL/6J mice at 6 weeks of age (20 to 22 g) were used in a normal control group and an ICS stress loading group.

Using "5'-AGCTGCCATGACAGTGCTGT-3' (SEQ ID NO:5)" as AS-ODN, BLAST search was performed; it was confirmed that the sequence thereof was specific for the LPA1 receptor. For comparative control, mice dosed with a missense oligodeoxynucleotide having a noncomplementary sequence (hereinafter, denoted as MS-ODN) and mice dosed with artificial cerebro-spinal fluid (ACSF) as Vehicle were used. Using "5'-AGCAGCGTTGTCACTGCAGT-3' (SEQ ID NO:6)" as MS-ODN, BLAST search was performed; it was confirmed that the sequence thereof was not similar to other receptors.

SART (ICS) stress based on Production Example 1 above was loaded on the mice after being given ODN and ACSF, after which pain threshold values were measured, and changes over days were examined.

Example 2

LPA2 AS-ODN-Treated Mice

Ten to twelve C57BL/6J mice at 6 weeks of age (20 to 22 g) were used in a normal control group and an ICS stress loading group.

Using "5'-TACTACAACGAGACCATCGG-3' (SEQ ID NO:7)" as AS-ODN, BLAST search was performed; it was confirmed that the sequence thereof was specific for the LPA1 receptor. For comparative controls, mice dosed with MS-ODN having a noncomplementary sequence and mice dosed with artificial cerebro-spinal fluid (ACSF) as Vehicle were used. Using "5'-CGATACACTAGAACGCTCGA-3' (SEQ ID NO:8)" as MS-ODN, BLAST search was performed; it was confirmed that the sequence thereof was not similar to other receptors.

SART (ICS) stress based on Production Example 1 above was loaded on the mice after being dosed with ODN and ACSF, after which pain threshold values were measured, and changes over days were examined.

Example 3

In Example 3, chronic pains were evaluated on mice loaded with stress based on Production Example and Examples. Regarding how to evaluate chronic pains, pain threshold values were evaluated over days by a mechanical stimulus-induced pain test. The mechanical stimulus-induced pain test was performed according to the digitized von Frey method.

<Method 1>
Method of Treatment with AS-ODN

AS-ODN was given by intracerebroventricular administration at 10 μg once daily, starting five days before SART (ICS) stress loading. After pretreatment for 5 consecutive days, SART (ICS) stress was started, and intracerebroventricular administration was performed once a day even during the stress loading period. However, there was no administration on day 3 of stress loading, after which administration was discontinued; a total of 7 administrations were performed. The single-dose volume was 5 μl.

In the same way as the above-described method of treatment, MS-ODN and Vehicle were administered 7 times in total before stress loading and during the stress loading period.

<Method 2>
Mechanical Stimulus-Induced Pain Test

On mice acclimated to the environment on a 5 mm×5 mm-mesh net (adaptation-applied), a custom-made plastic chip was applied to a planta of each mouse under a constant pressure from below. At that time, responding weight threshold values were measured digitally.

Figure 2:
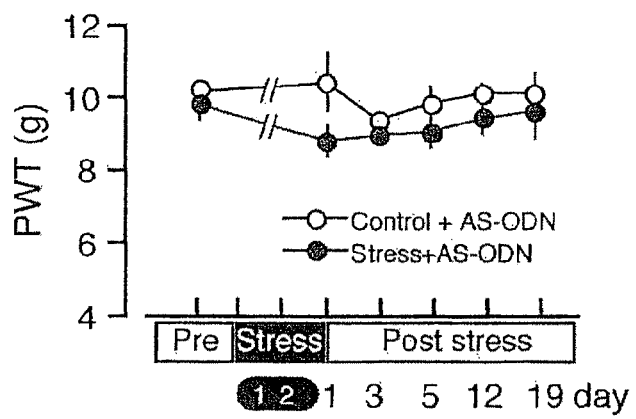
FIG. 2 is a graphic representation showing results of the mechanical stimulus-induced pain test of Example 3 performed on the AS-ODN-treated mice of Example 1.
Figure 3:
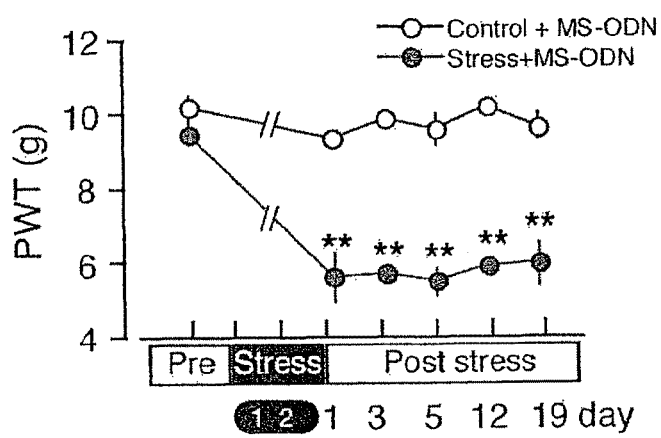
FIG. 3 is a graphic representation showing results of the mechanical stimulus-induced pain test of Example 3 performed on the MS-ODN-treated mice of Example 1.

<Results 1>
FIGS. 1 to 3 show results of measurements of pain threshold values over days in the mice given the LPA1 receptor AS-ODN in Example 1; FIG. 1 shows the observed results for the Vehicle treatment group, FIG. 2 for the AS-ODN treatment group, and FIG. 3 for the MS-ODN treatment group.

In FIGS. 1 to 3, the vertical axis (PWT) indicates measured weight threshold value (g). The transverse axis indicates the number of days that elapsed before the start of ICS stress loading (Pre), during the stress loading period (Stress), and after stress loading (Post stress). In FIGS. 1 to 3, "stress (●)" indicates the stress loading group and "control (○)" indicates the normal control group.

As shown in FIG. 1, when SART (ICS) stress was given to mice previously treated by Vehicle administration, the mice that exhibited a value of 9.44±0.2 g on the day before stress loading responded at 6.14±0.2 g on day 1 of stress loading. A pain threshold value reduction due to the stress was confirmed, at which time a significant difference was noted compared with the pain threshold value of 10.06±0.3 g for the normal control group. This hypersensitive response persisted for at least 19 days or more, and was chronic.

As shown in FIG. 2, the SART (ICS) stress loading group treated with LPA1 AS-ODN in Example 1 exhibited a value of 9.77±0.4 g on the day before stress loading, with no difference observed from the value for the Vehicle group obtained on the day before stress loading. On day 1 of stress loading, the threshold value for the AS-ODN treatment group was 8.76±0.5 g; the hypersensitive response observed with Vehicle was not observed. Statistical processing revealed no significant difference from the AS-ODN-treated normal control group; rather, the results showed suppression of the threshold value reduction in the Vehicle-treated stress group. Even measurements were made over days, no hypersensitive responses were noted.

As shown in FIG. 3, when SART (ICS) stress was given to mice previously treated by MS-ODN administration, the mice that exhibited a value of 9.59±0.3 g on the day before stress loading responded at 5.68±0.7 g on day 1 of stress loading. A reduction in the pain threshold by the stress was confirmed, at which time a significant difference was noted compared with the pain threshold value of 9.49±0.2 g for the normal control group. This hypersensitive response persisted for at least 19 days or more, and was chronic.

According to the results of Example 1 and Example 3, it was found that when SART (ICS) stress was given to mice previously dosed with LPA1 AS-ODN to suppress the expression, chronic pains, which were observed in both the Vehicle treatment group and the LPA1 MS-ODN treatment group, were suppressed. However, the threshold values for the normal control group dosed with AS-ODN were comparable to those for the Vehicle treatment group and the LPA1 MS-ODN treatment group.

Figure 4:
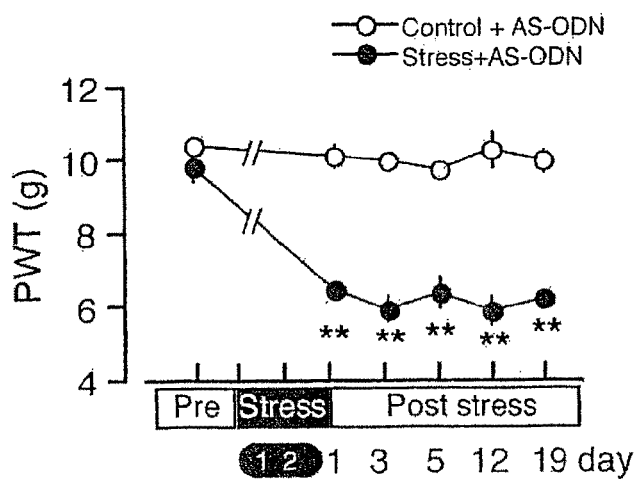
FIG. 4 is a graphic representation showing results of the mechanical stimulus-induced pain test of Example 3 performed on the AS-ODN-treated mice of Example 2.
Figure 5:
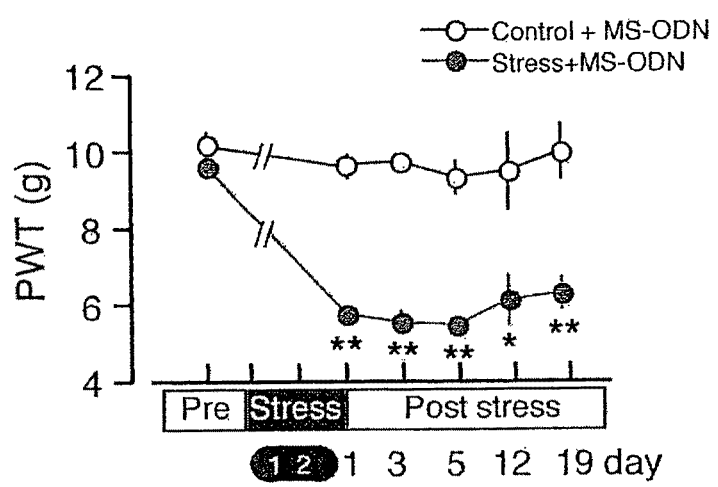
FIG. 5 is a graphic representation showing results of the mechanical stimulus-induced pain test of Example 3 performed on the MS-ODN-treated mice of Example 2.

<Results 2>
FIGS. 4 and 5 show results of measurements of pain threshold values over days in the mice dosed with the LPA2 receptor AS-ODN in Example 2; FIG. 4 shows the observed results for the AS-ODN treatment group, and FIG. 5 for the MS-ODN treatment group.

In FIGS. 4 and 5, the vertical axis (PWT) indicates measured weight threshold value (g). The transverse axis indicates the number of days that elapsed before the start of ICS stress loading (Pre), during the stress loading period (Stress), and after stress loading (Post stress). In FIGS. 4 and 5, "stress (●)" indicates the stress loading group, and "control (○)" indicates the normal control group.

As shown in FIG. 4, the SART (ICS) stress loading group treated with LPA2 AS-ODN in Example 2 exhibited a value of 9.77±0.5 g on the day before stress loading; no difference was observed from the value for the Vehicle group on the day before stress loading, shown in FIG. 1. On day 1 of stress loading, the threshold value for the AS-ODN treatment group was 6.43±0.1 g, showing a reduction in threshold value, i.e., a hypersensitive response. Statistical processing revealed a significant difference compared with the AS-ODN-treated normal control group. This hypersensitive response persisted for at least 19 days.

As shown in FIG. 5, when SART (ICS) stress was given to mice previously treated by MS-ODN administration, the mice that exhibited a value of 9.58±0.3 g on the day before stress loading responded at 5.79±0.1 g on day 1 of stress loading. A reduction in the pain threshold value by the stress was confirmed, at which time a significant difference was noted compared with the pain threshold value of 9.65±0.3 g for the normal control group. This hypersensitive response persisted for at least 19 days, and was chronic.

According to the results of Example 2 and Example 3, it was found that when SART (ICS) stress was given to mice previously dosed with LPA2 AS-ODN to suppress the expression of LPA2, no suppression of SART (ICS) stress-induced pains was noted as in the LPA1 AS-ODN treatment group, which exhibited a hypersensitive response comparable to that for the Vehicle group.

Judging from the results of Example 1 and Example 2, it can be thought that the pains induced by repeated cold temperature stress are more largely involved by the LPA1 receptor than by the LPA2 receptor. For this reason, suppression of stress-induced pains with LPA1 receptor-specific antibodies, antisense nucleic acids, inhibitors and the like is likely. The stress model is believed to be a possible animal experimental model of fibromyalgia, and considering the results of the present invention, it is expected to find an application for the treatment of fibromyalgia.

(Experimental Animals, Experimental Environment and Rearing Environment)

In the Examples below, male C57BL/6J mice at 6 weeks of age (20 to 25 g) were used. These mice were reared in a room set at a room temperature of 22±2° C. and a humidity of 55±5% under natural conditions in both the daytime and nighttime. The mice were allowed to take water (tap water) and a solid food (MF, Oriental Yeast, Tokyo) ad libitum.

Regarding the experimental environment, the experiments were performed using a room in a laboratory under constant temperature (22±2° C.) and constant humidity (55±5%) conditions. The mice to be used in the experiments were transferred to the room by 24 hours before the start of the experiments, reared under natural management in both the daytime and nighttime, and allowed to take a food and tap water ad libitum as described above. The experiments were performed between 10 a.m. and 17 p.m.

All the experiments were performed in compliance with the Guidelines for Animal Experimentation, Nagasaki University, and the method specified by the International Committee on Pain Experiments (Animal Experiment Permission Number: 0706130596).

Example 4

Drug Administration

1) ATX-Antisense

ATX-antisense is a drug that suppresses the synthesis of the mRNA of ATX, an LPA synthetase. The ATX-antisense (ATX-AS) used was designed to have the base sequence: "5'-GTC TTG CCA TGC CGA GGG AT-3' (SEQ ID NO:13)", and the ATX-missense (ATX-MS) used was designed to have the base sequence: "5'-GTT CTC GCA GTC GCA GGA GT-3' (SEQ ID NO:14)". The dosage was 10 µg/µl both for the antisense and for the missense.

Figure 8:
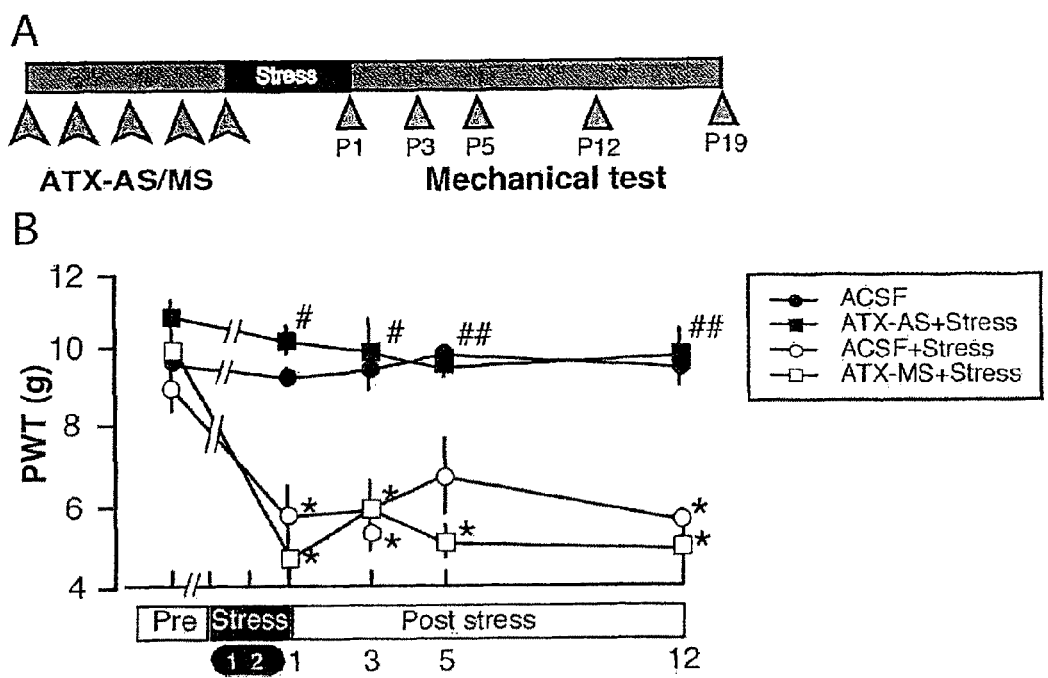
FIG. 8 is a graphic representation showing changes over days in mechanical nociceptive responses to intracerebroventricular administration of ATX-AS to C57BL/6J. A: A plan for ATX-AS/MS administration is shown. Intracerebroventricular administration was performed, starting on 5 days before, including the starting day of ICS stress loading. B: Changes over days in mechanical nociceptive responses are shown. ACSF group: n=3, ACSF+ICS stress group: n=4, ATX-MS+ICS stress group: n=3, ATX-AS+ICS stress group: n=4. ## indicates $P<0.01$ when comparing the ATX-AS group and the ATX-MS group; * indicates $P<0.05$ when comparing the ATX-AS group and the ATX-MS group.

ATX-antisense (operon, 3170003) was given by intracerebroventricular administration on consecutive days starting five days previously, including days of stress loading (FIG. 8A). Doses were given in solution in artificial cerebro-spinal fluid. For control groups, the same amounts of ATX-missense (operon, 3170004) and the solvent were administered, respectively. Using a 50 µl Hamilton microsyringe and a needle-equipped cannula, a total volume of 5 µl was given by intracerebroventricular administration. A 26-gauge needle for intracerebroventricular administration was used.

2) PLA2 Inhibitor

Figure 9:
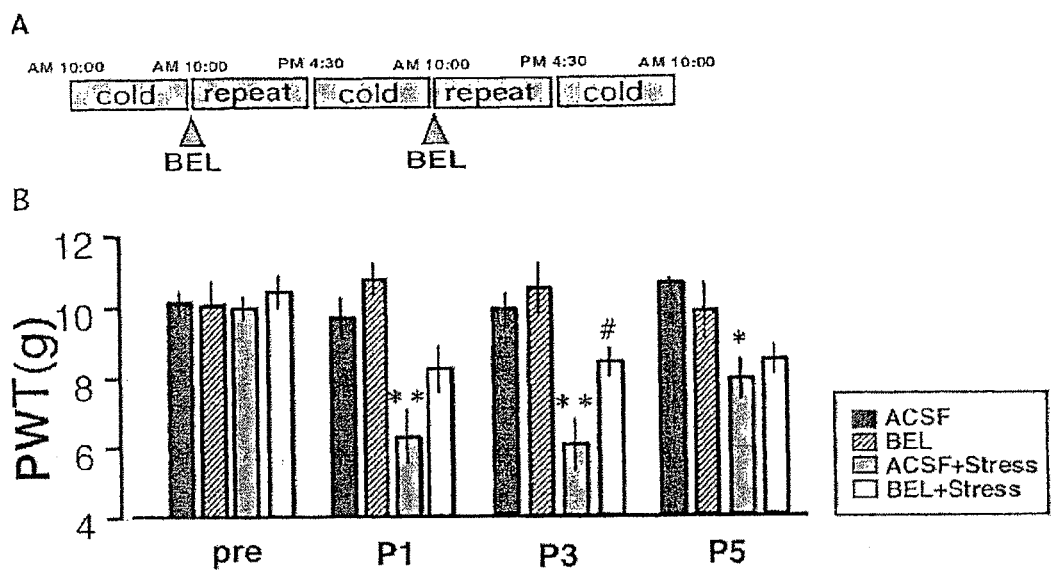
FIG. 9 is a graphic representation showing changes over days in mechanical nociceptive responses to intracerebroventricular administration of Bromoenol lactone (BEL) to C57BL/6J. A: A plan for BEL administration is shown. B: Changes over days in mechanical nociceptive responses are shown. ACSF group: n=4, BEL group: n=5, ACSF+ICS stress group: n=8, BEL+ICS stress group: n=8. ** indicates $P<0.01$ when comparing the ACSF group and the ACSF+ICS stress group; * indicates $P<0.05$ when comparing the ACSF group and the ACSF+ICS stress group.

As a PLA2 inhibitor, Bromoenol lactone (Cayman chemical) was used. Drug administration was performed twice in total at 10 a.m. before performing repeated cold stimulation in stress loading (FIG. 9A).

The whole amount of 5 mg of the drug was dissolved in 200 µl of DMSO and dispensed at 20 nmol/10 µl. 384 µl of artificial cerebro-spinal fluid was added thereto. For a control group, the same amounts of DMSO and artificial cerebro-spinal fluid were mixed and administered. Using a 50 µl Hamilton microsyringe and a needle-equipped cannula, a total volume of 5 µl was given by intracerebroventricular administration. A 26-gauge needle for intracerebroventricular administration was used.

Example 5

Creation of SART (ICS) Model and CCS Model

To create a mouse model of fibromyalgia, ICS (Intermittent Cold Stress) was loaded. Regarding mouse rearing environmental temperatures, the animals were reared with repeated alterations of room temperature (24±2° C.) and low temperature (4±2° C.) every 30 minutes in the daytime, and at low temperature in the nighttime. To avoid excess moisture in the rearing environment, a cage was placed upsidedown on a cage mesh, and a gap was made between the cage and the mesh using fractions of a solid food for ordinary experimentation (MF, Oriental Yeast, Tokyo). The animals were allowed to take a solid food and water in the form of tap water solidified with agar and cut into about 1 cm cubes ad libitum, and reared at constant humidity (55±5%) under natural conditions in both the daytime and nighttime. Two or one mouse was reared in each cage.

On the starting day, at 16:30, the mice were transferred to a refrigerator under low temperature conditions (4° C.); they were reared until 10:00 on the following day. At 10:00, the animals were returned to room temperature, after which they were reared until 16:30 with repeated alterations of low temperature conditions and room temperature conditions every 30 minutes. This day was established as the starting day of repeated stress, taken as day 1 of stress loading. From 16:30 to 10:00 on day 2 of stress loading, the animals were reared at 4° C. as on the day before stress loading. On day 2, repeated stress was given in the same way as on day 1. At 10:00 on day 3, the animals were returned to room temperature to finish. The day of completion was taken as P1 (Post Stress day 1).

A control group (Control) was reared constantly at room temperature during the same period (from 16:30 on the day before stress loading to 10:00 on day 3) for 3 days.

CCS model mice were reared constantly at low temperature during the same period (from 16:30 on the day before stress loading to 10:00 on day 3) for 3 days (Molecular Pain 6, 4:52 November 2008).

Example 6

Blood Collection in Measuring Corticosterone Concentrations

Serum corticosterone was collected at P1, P5, P12 and P19. Each mouse was decapitated, and all the blood was gathered. After the collection, the blood was applied to a centrifuge at 3000 rpm for 30 minutes to separate the plasma. The supernatant was collected, frozen in dry ice, and stored at −80° C. until analysis. Blood sampling was performed between 21:00 and 22:00, when the concentration was highest, in synchronization with the rhythm of diurnal change in corticosterone in the blood.

Example 7

How to Evaluate Pain-Related Behavior

The test methods 1) to 2) below were performed to obtain measurements at an interval of about 10 minutes. This was to prevent tissue damage due to the continuous measurement. 1) Automated Digitized Von Frey Test: Mechanical Nociception Test Method Prior to the experiment, each mouse was placed on a rack on a mesh and covered with a cage from above, and the animal was acclimated to the same environment as the experiment for not less than 1 hour. The tip of a plastic chip was pressed vertically against the center of a hind paw of the mouse from below the rack; when the mouse behaved to withdraw the hind leg, the automatically measured value was read. Intensity of stimulation was set at a level such that the weight would be around 10 g for a normal mouse. Three measurements or more were made, and the mean value was adopted.

2) Hargreaves Test (Thermal Paw-Withdrawal Test): Thermal Nociception Test Method Prior to the experiment, each mouse was placed on a glass plate and covered with a cage from above, and the animal was acclimated to the same environment as the experiment for not less than 1 hour. A thermal stimulus was given to a hind paw of the mouse; when the mouse behaved to escape the stimulus, the automatically measured value was read. The stimulating beam was set at a level such that the measurement would be around 10 seconds for a normal mouse. To avoid tissue damage, a cutoff time was set at 20 seconds. Three measurements or more were made, and the mean value was adopted.

3) Evaluation of Hyperalgesia Over Days

With the day of completion of ICS loading as P1, pain threshold values were measured on P3, P5, P12 and P19.

Example 8

Statistical Processing

All data were statistically analyzed using Sheffe's F test. If a test by one-way layout analysis of variance revealed a difference between levels, a multiple comparison test was performed to determine the groups between which a difference was present. If one * or # mark is obtained, the significance level was determined to be 5% or less; if two marks are obtained, the significance level was determined to be less 1% or less. All results are expressed as (mean)±S.E.M.

<Results 3>

1) Hypersensitive Responses Over Days to Mechanical Stimulation in ICS

Figure 6:
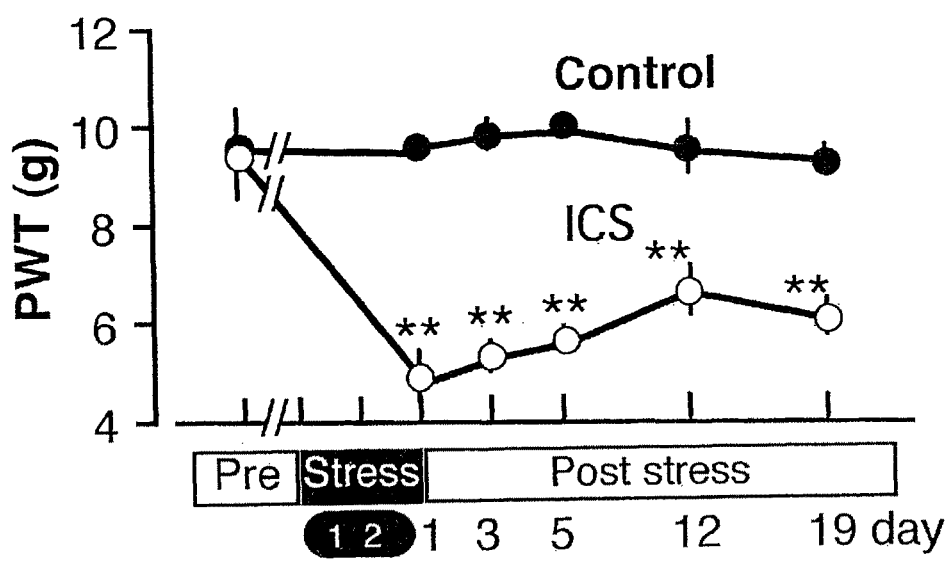
FIG. 6 is a graphic representation showing hypersensitive responses over days to mechanical stimulation in ICS. Control group: n=4, ICS stress group: n=6. ** indicates $P<0.01$ when comparing the control stress group and the ICS stress group.

After completion of stress loading, for both the ICS group and the control group, observations were continued over days on the schedule of P1, P3, P5, P12, and P19. Pains were evaluated on a right leg of each mouse using the mechanical nociception test method (FIG. 6). Before performing stress loading, no difference was seen between the threshold values for the control group and the ICS group. After completion of stress loading, there was a significant difference between the ICS group and the control group (P<0.01). At P1, the threshold value was 9.5±0.2 g for the control group and 4.8±0.5 g for the ICS group; until P19, persistent reductions in threshold value were confirmed (control group: 9.1±0.3 g, ICS group: 5.9±0.4 g). This hypersensitive response was of the same degree as the threshold values exhibited by a neuropathic pain model undergoing partial ligation of the sciatic nerve at our laboratory.

The following two observations were obtained during the creation of the models. First, the ICS group seemed to have greater food consumption than the control group, and this was particularly evident just after a change in the temperature environment. This may represent an adaptive phenomenon to prevent body temperature falls by increasing food consumption to have a pyrogenic effect. Second, body weight tended to decrease in the ICS group during the stress loading period. However, the body weight exhibited a recovering tendency after completion of stress loading, the recovery being to the same extent as the control group. Regarding the behavior of other animals, there was no difference from the control group.

2) Corticosterone Concentrations in ICS/CCS

Figure 7:
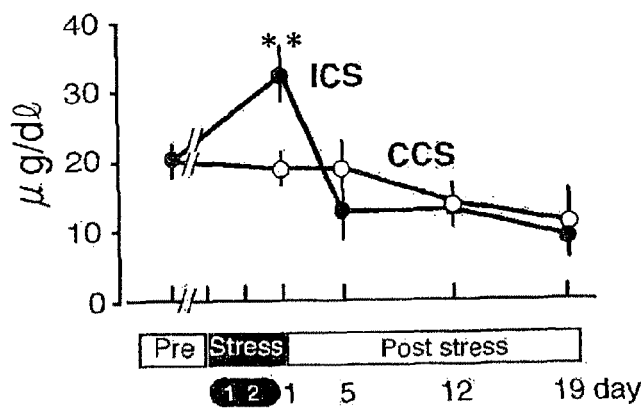
FIG. 7 is a graphic representation showing results of measurements of corticosterone concentration for ICS/CCS stress model mice. ICS stress group: n=3, CCS group: n=6; ** indicates $P<0.01$ when comparing the CCS stress group and the ICS stress group.

As an index of stress loading, blood corticosterone concentrations were measured. Concentration measuring samples were collected on days 1, 5, 12, and 19 after completion of stress loading. On day 1 after completion of repeated stress loading, the corticosterone concentration for the ICS group was 32.7±4.1 µg/dl, showing a significant elevation compared with the concentration for the control (CCS) group (10.0±2.4 µg/dl) (FIG. 7). However, regarding the changes over days, the concentration elevation for the ICS group was no longer observed on day 5 after completion of stress loading. Thereafter, both the ICS group and the control group exhibited a value of about 10 µg/dl. Judging from this result, it can be thought that the animals were stressed by the repeated cold stress, whereas the animals were not chronically stressed by the continuous cold stress to the extent that caused an elevation of corticosterone concentration.

A difference was found when creating the mouse models of ICS and CCS. Both food consumption and the amount of behavior were larger in ICS. In particular, regarding food consumption, ICS often exhibited the behavior of eating food just after the temperature change was given every 30 minutes. Regarding the amount of behavior, the CCS animals tended to stay at one place, but no abnormal behavior was seen.

3) Responses to Nociceptive Stimulus by Intracerebroventricular Administration of ATX-AS in Male C57BL/6J mice Recently, Nishiyori and Ueda reported that hyperalgesia and hyperpathia such as allodynia in an ICS stress model were suppressed over a long period of 4 days by intracerebroventricular administration of a small amount of gabapentin (Molecular Pain 6, 4:52 Nov. 2008). Gabapentin is a drug with Ca$\alpha2\delta$-1 as a molecular target. Ca$\alpha2\delta$-1 was shown to be expressed in myelinated fiber A in nerve injuries that induce neuropathic pains, and in applying the causal molecule LPA to the spinal subarachnoidal cavity, and to be one of responsible molecules for neuropathic pains (Yasashii Itami Gaku, Hiroshi Ueda, Kazuo Toda, Brain Shuppan, pp. 89-90; Nature Medicine Volume. 10, Number. 7, July 2004, pp. 712-718; Mol. Pain. 2008 Apr. 1; 4:11. Review). Hence, the possible production of LPA in the brain was assumed in the ICS stress model, like in a nociceptive neuropathic pain model. In this experiment, the LPA synthetase inhibitor ATX-AS was given by intracerebroventricular administration for consecutive days starting 5 days previously, including the starting day of stress loading, and the effect on the development of hyperpathia was evaluated (FIG. 8A). A mechanical nociception test method was performed on days 1, 3, 5, and 12 after completion of stress loading, and an electrical nociception test method on days 5 and 6. In the two tests, a significant difference (P<0.05) was noted between the artificial cerebrospinal fluid (ACSF)+stress group and the ACSF group.

3-1) Changes Over Days in Mechanical Nociceptive Responses

In the ACSF control group and the ATX-MS dosing group, significant reductions of mechanical nociceptive response threshold values were observed from P1 to P12 after ICS stress loading. By contrast, in the ATX-AS dosing group, almost no threshold value changes were noted with ICS stress. Comparing the ATX-MS dosing group and the ATX-AS dosing group, a significant difference was observed from P1 to P12.

Figure 10:
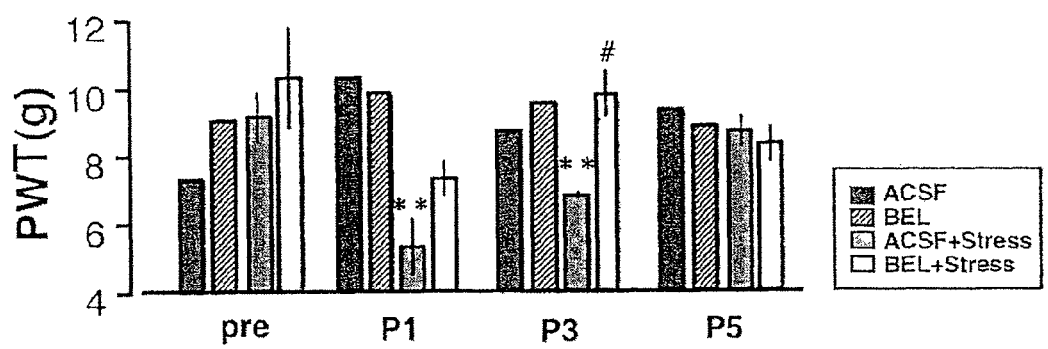
FIG. 10 is a graphic representation showing changes over days in thermal nociceptive responses to intracerebroventricular administration of Bromoenol lactone (BEL) to C57BL/6J. ACSF group: n=2, BEL group: n=2, ACSF+ICS stress group: n=4, BEL+ICS stress group: n=4. ** indicates $P<0.01$ when comparing the ACSF group and the ACSF+ICS stress group.

4) Responses to Nociceptive Stimulation by Intracerebroventricular Administration of Bromoenol Lactone (BEL) in Male C57BL/6J Mice Bromoenol lactone (BEL) is a PLA2 inhibitor. The pathway is of lysophosphatidylcholine (LPC) production from phosphatidylcholine by phospholipase A2 (PLA2) and subsequent production of LPA by ATX is reportedly the most important to the process of LPA production. While hypersensitivity persists in ICS model mice, transient hypersensitivity is seen in the CCS model mice. This leads to the notion that repeated normal-and-low-temperature stimulation is associated with the development of hypersensitivity in the ICS model mice. For this reason, dosing took place at 10 am, just before giving repeated cold stimulation (FIG. 9A). On days 1, 3, and 5 after completion of stress loading, pain threshold values were examined by the mechanical nociception test method (FIG. 9B) and the thermal nociception test method (FIG. 10).

4-1) Changes Over Days in Mechanical Nociceptive Responses

Referring to FIG. 9B, reductions of mechanical nociceptive response threshold values due to ICS stress tended to be suppressed by BEL administration between P1 and P5, with a significant change at P3.

4-2) Changes Over Days in Thermal Nociceptive Responses

Referring to FIG. 10, thermal hyperalgesia due to ICS stress tended to be suppressed by BEL administration between P1 and P5, with a significant change at P3.

INDUSTRIAL APPLICABILITY

According to a therapeutic or prophylactic agent for generalized pain disease of the present invention, it is possible to make a major contribution to the establishment of an effective and reliable therapeutic policy and prophylactic method for generalized pain disease, for which no therapies have been established to date because the cause remains unclear.

This application is based on patent application Nos. 2008-204762 (filing date: Aug. 7, 2008) and 2009-112990 (filing date: May 7, 2009) filed in Japan, the contents of which are incorporated in full herein.

The invention claimed is:

1. A method of treating fibromyalgia in a subject comprising administering to the subject an effective amount of a low-molecular weight compound that binds to LPA1 to inhibit signaling, thereby treating fibromyalgia in the subject.

* * * * *

SEQUENCE LISTING

<160> NUMBER OF SEQ ID NOS: 14

<210> SEQ ID NO 1
<211> LENGTH: 3104
<212> TYPE: DNA
<213> ORGANISM: Homo sapiens
<220> FEATURE:
<221> NAME/KEY: CDS
<222> LOCATION: (349)..(1443)

<400> SEQUENCE: 1

```
acggcgcgct gggctcacac tgtcccgccg cggacgggct ttgtggttgg gggcgcgcgt      60
gcgagtgcca gtgagagtgt gggtgcgcgc tgtgggccgc ggcgcgggtg ggtggccgtg     120
cgttcttgcg agccggcctg caggaggcga ggctcccctg gcctcccgca cccagcggcg     180
gaccgagccc ctggagggaa gttgccgcag ccgcccgggc cgccggcccct cctgtcccgc    240 gccaggtaca cagcttctcc tagcatgact tcgatctgat cagcaaacaa gaaaatttgt     300
ctcccgtagt tctgggggcgt gttcaccacc tacaaccaca gagctgtc atg gct gcc      357
                                                     Met Ala Ala
                                                       1 atc tct act tcc atc cct gta att tca cag ccc cag ttc aca gcc atg       405
Ile Ser Thr Ser Ile Pro Val Ile Ser Gln Pro Gln Phe Thr Ala Met
      5                  10                  15 aat gaa cca cag tgc ttc tac aac gag tcc att gcc ttc ttt tat aac       453
Asn Glu Pro Gln Cys Phe Tyr Asn Glu Ser Ile Ala Phe Phe Tyr Asn
 20                  25                  30                  35 cga agt gga aag cat ctt gcc aca gaa tgg aac aca gtc agc aag ctg       501
Arg Ser Gly Lys His Leu Ala Thr Glu Trp Asn Thr Val Ser Lys Leu
                 40                  45                  50 gtg atg gga ctt gga atc act gtt tgt atc ttc atc atg ttg gcc aac       549
Val Met Gly Leu Gly Ile Thr Val Cys Ile Phe Ile Met Leu Ala Asn
             55                  60                  65 cta ttg gtc atg gtg gca atc tat gtc aac cgc cgc ttc cat ttt cct       597
Leu Leu Val Met Val Ala Ile Tyr Val Asn Arg Arg Phe His His Phe Pro
         70                  75                  80 att tat tac cta atg gct aat ctg gct gct gca gac ttc ttt gct ggg       645
Ile Tyr Tyr Leu Met Ala Asn Leu Ala Ala Ala Asp Phe Phe Ala Gly
     85                  90                  95 ttg gcc tac ttc tat ctc atg ttc aac aca gga ccc aat act cgg aga       693
```

|   |   |   |   |   |   |   |   |   |   |   |   |   |   |   |   |
|---|---|---|---|---|---|---|---|---|---|---|---|---|---|---|---|
| Leu | Ala | Tyr | Phe | Tyr | Leu | Met | Phe | Asn | Thr | Gly | Pro | Asn | Thr | Arg | Arg |
| 100 |   |   |   |   | 105 |   |   |   | 110 |   |   |   |   | 115 |   |

```
ctg act gtt agc aca tgg ctc ctt cgt cag ggc ctc att gac acc agc     741
Leu Thr Val Ser Thr Trp Leu Leu Arg Gln Gly Leu Ile Asp Thr Ser
            120                 125                 130 ctg acg gca tct gtg gcc aac tta ctg gct att gca atc gag agg cac     789
Leu Thr Ala Ser Val Ala Asn Leu Leu Ala Ile Ala Ile Glu Arg His
                135                 140                 145 att acg gtt ttc cgc atg cag ctc cac aca cgg atg agc aac cgg cgg     837
Ile Thr Val Phe Arg Met Gln Leu His Thr Arg Met Ser Asn Arg Arg
        150                 155                 160 gta gtg gtg gtc att gtg gtc atc tgg act atg gcc atc gtt atg ggt     885
Val Val Val Val Ile Val Val Ile Trp Thr Met Ala Ile Val Met Gly
    165                 170                 175 gct ata ccc agt gtg ggc tgg aac tgt atc tgt gat att gaa aat tgt     933
Ala Ile Pro Ser Val Gly Trp Asn Cys Ile Cys Asp Ile Glu Asn Cys
180                 185                 190                 195 tcc aac atg gca ccc ctc tac agt gac tct tac tta gtc ttc tgg gcc     981
Ser Asn Met Ala Pro Leu Tyr Ser Asp Ser Tyr Leu Val Phe Trp Ala
                200                 205                 210 att ttc aac ttg gtg acc ttt gtg gta atg gtg gtt ctc tat gct cac    1029
Ile Phe Asn Leu Val Thr Phe Val Val Met Val Val Leu Tyr Ala His
            215                 220                 225 atc ttt ggc tat gtt cgc cag agg act atg aga atg tct cgg cat agt    1077
Ile Phe Gly Tyr Val Arg Gln Arg Thr Met Arg Met Ser Arg His Ser
        230                 235                 240 tct gga ccc cgg cgg aat cgg gat acc atg atg agt ctt ctg aag act    1125
Ser Gly Pro Arg Arg Asn Arg Asp Thr Met Met Ser Leu Leu Lys Thr
245                 250                 255 gtg gtc att gtg ctt ggg gcc ttt atc atc tgc tgg act cct gga ttg    1173
Val Val Ile Val Leu Gly Ala Phe Ile Ile Cys Trp Thr Pro Gly Leu
260                 265                 270                 275 gtt ttg tta ctt cta gac gtg tgc tgt cca cag tgc gac gtg ctg gcc    1221
Val Leu Leu Leu Leu Asp Val Cys Cys Pro Gln Cys Asp Val Leu Ala
                280                 285                 290 tat gag aaa ttc ttc ctt ctc ctt gct gaa ttc aac tct gcc atg aac    1269
Tyr Glu Lys Phe Phe Leu Leu Leu Ala Glu Phe Asn Ser Ala Met Asn
            295                 300                 305 ccc atc att tac tcc tac cgc gac aaa gaa atg agc gcc acc ttt agg    1317
Pro Ile Ile Tyr Ser Tyr Arg Asp Lys Glu Met Ser Ala Thr Phe Arg
        310                 315                 320 cag atc ctc tgc tgc cag cgc agt gag aac ccc acc ggc ccc aca gaa    1365
Gln Ile Leu Cys Cys Gln Arg Ser Glu Asn Pro Thr Gly Pro Thr Glu
325                 330                 335 ggc tca gac cgc tcg gct tcc tcc ctc aac cac acc atc ttg gct gga    1413
Gly Ser Asp Arg Ser Ala Ser Ser Leu Asn His Thr Ile Leu Ala Gly
340                 345                 350                 355 gtt cac agc aat gac cac tct gtg gtt tag aacggaaact gagatgagga    1463
Val His Ser Asn Asp His Ser Val Val
                360 accagccgtc tctcttgga ggataaacag cctcccccta cccaattgcc agggcaaggt   1523 ggggtgtgag agaggagaaa agtcaactca tgtacttaaa cactaaccaa tgacagtatt   1583 tgttcctgga ccccacaaga cttgatatat attgaaaatt agcttatgtg acaaccctca   1643 tcttgatccc catcccttct gaaagtagga agttggagct cttgcaatgg aattcaagaa   1703 cagactctgg agtgtccatt tagactacac taactagact tttaaaagat ttgtgtggt   1763 ttggtgcaag tcagaataaa ttctggctag ttgaatccac aacttcattt atatacaggc   1823
```

```
ttcccttttt tattttttaaa ggatacgttt cacttaataa acacgtttat gcctatcagc   1883
atgtttgtga tggatgagac tatggactgc ttttaaacta ccataattcc attttttccc   1943
ttacatagga aaactgtaag ttggaattat cttttgttta gaaagcatgc atgtaatgta   2003
tgtatgcagt atgccttact taaaaagatt aaaaggatac taatgttaaa tcttctagga   2063
aatagaacct agacttcaaa gccagtattt gtttaggtca tgaagcaaac aatgctctaa   2123
tcacaatatt aactgtttaa ttaaaatgtt gtaacaagta taaacagggg aatgtaagtt   2183
tattaccaaa gtgatatgta ttccaaaaaa gtcatagaag atgaagcact ataatattgt   2243
tcccatatat ttaaaatacc caagtacatt ctaattacca gtatatcaga ggaaaatttt   2303
cgtagtcttt gtaaaataat atactcatca tagaaaactt gaaaaatgca gaaatgtata   2363
aaaaagcaaa aatgattact gataatatca aacccagaa gtaaccacct ttaaaaagca    2423 accccccatgt atgcctatat gtgtattgta actttttttt acataattgg agtcatactg   2483
taaacagttt tataagtaga tcttttttcat tgcaaaattg ccacattttc ttatggcatt   2543
aaaaatttta caaaaacata attttaatgg ctatattata ttccatttaa tggatgcaac   2603
tcagtttatt taaccattcc catgttgtta actatttagg ttgtttctaa ttttcattat   2663
tataaagttg cagaaatttg gtgtacataa aactgtctcc atataattga ttattaggat   2723
atattcccat gaaggattct ttttttaaaa aaatgtgaaa tgtcatcttg tacttacacc   2783
tttcatgaaa agggatttcc tgcttttgta ctgcatgggt ggcagttgtg aggaaaagcc   2843
agtcaaatga cctttttaca aagaaatgc agtggtcact tcagttgaga gtgactttttt   2903 aatacaacaa gatcaactag aagaattcaa ctgtctcaag aatcaaggta ccccaatata   2963
tctcgcaatt ccaaactttg tttgagggac tcgttatcca gctcttggta gccacacctg   3023
caatgtaaaa tggaagaaaa tgcaaagaaa ccaaatgtgc cgagtgaata aaggattgtc   3083
atatcaaaaa aaaaaaaaaa a                                              3104
```

<210> SEQ ID NO 2  
<211> LENGTH: 364  
<212> TYPE: PRT  
<213> ORGANISM: Homo sapiens

<400> SEQUENCE: 2

```
Met Ala Ala Ile Ser Thr Ser Ile Pro Val Ile Ser Gln Pro Gln Phe
1               5                   10                  15

Thr Ala Met Asn Glu Pro Gln Cys Phe Tyr Asn Glu Ser Ile Ala Phe
            20                  25                  30

Phe Tyr Asn Arg Ser Gly Lys His Leu Ala Thr Glu Trp Asn Thr Val
        35                  40                  45

Ser Lys Leu Val Met Gly Leu Gly Ile Thr Val Cys Ile Phe Ile Met
    50                  55                  60

Leu Ala Asn Leu Leu Val Met Val Ala Ile Tyr Val Asn Arg Arg Phe
65                  70                  75                  80

His Phe Pro Ile Tyr Tyr Leu Met Ala Asn Leu Ala Ala Ala Asp Phe
                85                  90                  95

Phe Ala Gly Leu Ala Tyr Phe Tyr Leu Met Phe Asn Thr Gly Pro Asn
            100                 105                 110

Thr Arg Arg Leu Thr Val Ser Thr Trp Leu Leu Arg Gln Gly Leu Ile
        115                 120                 125

Asp Thr Ser Leu Thr Ala Ser Val Ala Asn Leu Leu Ala Ile Ala Ile
    130                 135                 140
```

```
Glu Arg His Ile Thr Val Phe Arg Met Gln Leu His Thr Arg Met Ser
145                 150                 155                 160

Asn Arg Arg Val Val Val Ile Val Val Ile Trp Thr Met Ala Ile
                165                 170                 175

Val Met Gly Ala Ile Pro Ser Val Gly Trp Asn Cys Ile Cys Asp Ile
            180                 185                 190

Glu Asn Cys Ser Asn Met Ala Pro Leu Tyr Ser Asp Ser Tyr Leu Val
        195                 200                 205

Phe Trp Ala Ile Phe Asn Leu Val Thr Phe Val Val Met Val Val Leu
    210                 215                 220

Tyr Ala His Ile Phe Gly Tyr Val Arg Gln Arg Thr Met Arg Met Ser
225                 230                 235                 240

Arg His Ser Ser Gly Pro Arg Arg Asn Arg Asp Thr Met Met Ser Leu
                245                 250                 255

Leu Lys Thr Val Val Ile Val Leu Gly Ala Phe Ile Ile Cys Trp Thr
            260                 265                 270

Pro Gly Leu Val Leu Leu Leu Asp Val Cys Cys Pro Gln Cys Asp
        275                 280                 285

Val Leu Ala Tyr Glu Lys Phe Phe Leu Leu Leu Ala Glu Phe Asn Ser
290                 295                 300

Ala Met Asn Pro Ile Ile Tyr Ser Tyr Arg Asp Lys Glu Met Ser Ala
305                 310                 315                 320

Thr Phe Arg Gln Ile Leu Cys Cys Gln Arg Ser Glu Asn Pro Thr Gly
                325                 330                 335

Pro Thr Glu Gly Ser Asp Arg Ser Ala Ser Ser Leu His Thr Ile
        340                 345                 350

Leu Ala Gly Val His Ser Asn Asp His Ser Val Val
        355                 360

<210> SEQ ID NO 3
<211> LENGTH: 3650
<212> TYPE: DNA
<213> ORGANISM: Mus musculus
<220> FEATURE:
<221> NAME/KEY: CDS
<222> LOCATION: (214)..(1308)

<400> SEQUENCE: 3
agcacagtgc tgccctccgt aggctccggg ttgtgctggg tgaggcttgg gttgggttgg      60
cccggcggct gcgtgaactg cggagctgga cctagcaggc ttacagttcc tcctagcatg     120
accgagatct gatcagccaa cccgcgcatt gcttttgtgt cctggcactg cagtgcaggg     180
ggcctcttca tcgccccaaa ctacagcact gtc atg gca gct gcc tct act tcc     234
                                   Met Ala Ala Ala Ser Thr Ser
                                    1               5 agc cct gta att tca cag ccc cag ttc aca gcc atg aac gaa caa cag     282
Ser Pro Val Ile Ser Gln Pro Gln Phe Thr Ala Met Asn Glu Gln Gln
        10                  15                  20 tgc ttc tac aat gag tct atc gcc ttc ttt tat aac cgg agt ggg aaa     330
Cys Phe Tyr Asn Glu Ser Ile Ala Phe Phe Tyr Asn Arg Ser Gly Lys
    25                  30                  35 tat cta gcc aca gaa tgg aac aca gtg agc aag ctg gtg atg gga ctg     378
Tyr Leu Ala Thr Glu Trp Asn Thr Val Ser Lys Leu Val Met Gly Leu
40                  45                  50                  55 ggc atc act gtt tgc gtg ttc atc atg ttg gcc aat ctc ctg gtc atg     426
Gly Ile Thr Val Cys Val Phe Ile Met Leu Ala Asn Leu Leu Val Met
                60                  65                  70
```

```
gtg gca atc tac gtc aac cgc cgc ttc cat ttc cct att tat tac ttg      474
Val Ala Ile Tyr Val Asn Arg Arg Phe His Phe Pro Ile Tyr Tyr Leu
             75                  80                  85 atg gcc aac ctg gct gct gca gac ttc ttc gct gga ttg gcc tac ttc      522
Met Ala Asn Leu Ala Ala Ala Asp Phe Phe Ala Gly Leu Ala Tyr Phe
             90                  95                 100 tac ctg atg ttc aat aca gga cct aat acc cgg aga ctg act gtt aac      570
Tyr Leu Met Phe Asn Thr Gly Pro Asn Thr Arg Arg Leu Thr Val Asn
            105                 110                 115 acg tgg ctc ctc cgg cag ggc ctc att gac acc agc ctg aca gct tct      618
Thr Trp Leu Leu Arg Gln Gly Leu Ile Asp Thr Ser Leu Thr Ala Ser
120             125                 130                 135 gtg gcc aac ctg ctg gct att gct atc gag agg cac atc acg gtt ttc      666
Val Ala Asn Leu Leu Ala Ile Ala Ile Glu Arg His Ile Thr Val Phe
                140                 145                 150 cgc atg cag ctc cat aca cga atg agc aac cgg cgc gtg gtg gtg gtg      714
Arg Met Gln Leu His Thr Arg Met Ser Asn Arg Arg Val Val Val Val
                155                 160                 165 att gta gtc atc tgg act atg gcc att gtg atg ggt gct atg ccc act      762
Ile Val Val Ile Trp Thr Met Ala Ile Val Met Gly Ala Met Pro Thr
                170                 175                 180 gtg ggc tgg aac tgc atc tgt gat atc gat cac tgt tcc aac atg gca      810
Val Gly Trp Asn Cys Ile Cys Asp Ile Asp His Cys Ser Asn Met Ala
185                 190                 195 ccc ctc tac agt gac tcc tac tta gtc ttc tgg gcc att ttc aac ctg      858
Pro Leu Tyr Ser Asp Ser Tyr Leu Val Phe Trp Ala Ile Phe Asn Leu
200                 205                 210                 215 gtg acc ttt gtg gtc atg gtg gtt ctc tac gct cac atc ttt ggc tat      906
Val Thr Phe Val Val Met Val Val Leu Tyr Ala His Ile Phe Gly Tyr
                220                 225                 230 gtt cgc cag agg act atg agg atg tct cgg cat agt tct gga ccc agg      954
Val Arg Gln Arg Thr Met Arg Met Ser Arg His Ser Ser Gly Pro Arg
                235                 240                 245 agg aat cgg gac acc atg atg agc ctt ctg aag act gtg gtc att gtg     1002
Arg Asn Arg Asp Thr Met Met Ser Leu Leu Lys Thr Val Val Ile Val
            250                 255                 260 ctt ggt gcc ttt att gtc tgc tgg act ccg gga ttg gtc ttg tta ttg     1050
Leu Gly Ala Phe Ile Val Cys Trp Thr Pro Gly Leu Val Leu Leu Leu
265                 270                 275 ctg gat gtg tgc tgc ccg cag tgc gat gtc ctg gcc tat gag aag ttc     1098
Leu Asp Val Cys Cys Pro Gln Cys Asp Val Leu Ala Tyr Glu Lys Phe
280                 285                 290                 295 ttc ctc ctc ctg gcc gag ttc aac tct gct atg aac ccc atc atc tac     1146
Phe Leu Leu Leu Ala Glu Phe Asn Ser Ala Met Asn Pro Ile Ile Tyr
                300                 305                 310 tcc tac cgc gac aaa gag atg agc gcc acc ttc agg cag atc ctg tgt     1194
Ser Tyr Arg Asp Lys Glu Met Ser Ala Thr Phe Arg Gln Ile Leu Cys
            315                 320                 325 tgc cag cgc aac gag aac cct aat ggc ccc acg gaa ggc tct gac cgc     1242
Cys Gln Arg Asn Glu Asn Pro Asn Gly Pro Thr Glu Gly Ser Asp Arg
            330                 335                 340 tct gcc tcc tcc ctc aac cac acc att ctg gct gga gtt cac agc aac     1290
Ser Ala Ser Ser Leu Asn His Thr Ile Leu Ala Gly Val His Ser Asn
345                 350                 355 gac cac tct gtg gtt tag aaggaagcca gccggcctct gtggatctgt            1338
Asp His Ser Val Val
360 gaaccccacc ctaccccca ttgccagggc aaggtgggga gccagaggag atgaggacac    1398 tcctgtactt aacactaacc aatggcagta tttgtcccta gacccaagag acttgaggat   1458
```

```
gaatttattt ggcaggcccc atcttctcct ttggaaaaca gaaggggacc gtcttgtggt    1518
ggaattgaga aatggactct ggggtgaccg tgtagcattc actaactaga cttaaaagat    1578
tttatgtggt ttggcttaag ccaggaaaaa aaaatctgct gaattgagta tacaatcgag    1638
tatacacagg cttccccttt aaagaacaaa caatacattg catttattaa tgagtatgtt    1698
tatgcctgac agcatgtttg tgatcgaaaa gactgctaaa ctgacataga tgagttgttt    1758
tttttttttt gttttttgtt ttttttttaca tgatggagga aaagtataaa ttagaatgat    1818
ttttgtgttt gtttagaaag caagcatgtg gtgtgtgtat tcagtatgcc tttctttaaa    1878
gataaaaggc cactattta aatcttctag ggaatagaag aatctagtaa aaaccagtat    1938
tcatttaggc tacaggaaaa accatatcct aatcaattac cttttaatta agtaatgaa    1998 atatacatga aaggcaaagt aatgtgagct tgtcacccaa agagtgtgtg ctctccaaac    2058
gctggaggag atgaagctgt agcgttgtcc ctgcatagtg aagatacccca cgtgcgttct    2118 cagtgccaga ccctcagtgg gacttgtttt aaagcctgtg gttttccaag ttagaaaata    2178
atacctactt actatagaaa acttgaaaat tgcagaactg tgtgaaaaaa gaaaaaagaa    2238
agaaagattg ctgatatacg acctggaagt agccatcttt ccctgctcac ccacgtatgc    2298
ctatagacat atattatata cctttttttt tttttacata atcgggttga tattgtaaaa    2358
tgttttgtaa cttttctttt cagaattgcc aggttttttct atggcatttt ttttcaaaaa    2418
cgttagcggc tatataatat tccatttaat ggatgcagct cagtttattt agtaccattc    2478
ctgtattgtt gactatgctt ttggcttttt tttcataata ttggaagaat cttgtgtata    2538 taaactttg ccagtatcat tgatgattta cttgggctcc attccatga aggacctact    2598 tttaaaatgt gaaatgtcct catgtgttgt cactttataa aaagggatat tctaccctca    2658
aactgcaggg gtgaccatgc tgacaaaaag ctcagaaatt acctttttac aaaagaaaca    2718
cagtggctac tttagttgcg aatgggttct tgacaagatg tttcccaata acccagaccc    2778
ttaacataac tagcaaattt actttagtag gaactggtga tcccttctg gacacaagaa    2838 aacacaaaga catcaagcat cagagtgaat ccagcaatgc agtaccaagc agcctgggtg    2898
gggtgtgcta gcaactggct gctgtgtggt ctccagcaat cacccaatgg acaccctgtg    2958
ttcagagatg cccagtacag tgtcctggag actaaggtct ctaatgtcat gctatgagga    3018
acaaggagga agaagaatag tcctgaagca ggtgtggaga ggtcaggagg acgtctgaga    3078
gaaggcagtc ctgccaagag tggcattcta gggaggagga aggcagggtg tggcttgtgt    3138
ctggacagtc agtggtaggc atgtgacatt tgcctggtgg aaaaaaaata agtaggcgga    3198
gatccagtta gcaggacaaa gattttgctc gaggattccc ccaatccaag aaatttaaac    3258
tggaaatgag tgaaccgaac ttggactttt attgattccc cttttatggg ggaggtaagg    3318
actatttgaa ttgaaaagca tactaattga accttaataa atcattctca atcagtgttt    3378
ggcgatgtgt ggttctggtc tgtgcttttt ttctattttc gagaagcctc tggctgtgct    3438
gtgatggctt ctctctctga ccttctttaa cagtctgagg cagcccaaca actgttcctt    3498
tagctcagat actggttcct catccatgag attcatgaga gacgtgttac ctcaatggaa    3558
tgagtactag agcaaggtat ttagagagat tttttttatt atttatttat ttattttgaa    3618
taaaatgtat gtaataaata agataaaata aa                                  3650
```

<210> SEQ ID NO 4
<211> LENGTH: 364
<212> TYPE: PRT

<213> ORGANISM: Mus musculus

<400> SEQUENCE: 4

```
Met Ala Ala Ser Thr Ser Pro Val Ile Ser Gln Pro Gln Phe
1               5                   10                  15

Thr Ala Met Asn Glu Gln Gln Cys Phe Tyr Asn Glu Ser Ile Ala Phe
            20                  25                  30

Phe Tyr Asn Arg Ser Gly Lys Tyr Leu Ala Thr Glu Trp Asn Thr Val
                35                  40                  45

Ser Lys Leu Val Met Gly Leu Gly Ile Thr Val Cys Val Phe Ile Met
50                  55                  60

Leu Ala Asn Leu Leu Val Met Val Ala Ile Tyr Val Asn Arg Arg Phe
65                  70                  75                  80

His Phe Pro Ile Tyr Tyr Leu Met Ala Asn Leu Ala Ala Ala Asp Phe
                85                  90                  95

Phe Ala Gly Leu Ala Tyr Phe Tyr Leu Met Phe Asn Thr Gly Pro Asn
                100                 105                 110

Thr Arg Arg Leu Thr Val Asn Thr Trp Leu Leu Arg Gln Gly Leu Ile
                115                 120                 125

Asp Thr Ser Leu Thr Ala Ser Val Ala Asn Leu Leu Ala Ile Ala Ile
130                 135                 140

Glu Arg His Ile Thr Val Phe Arg Met Gln Leu His Thr Arg Met Ser
145                 150                 155                 160

Asn Arg Arg Val Val Val Val Ile Val Val Ile Trp Thr Met Ala Ile
                165                 170                 175

Val Met Gly Ala Met Pro Thr Val Gly Trp Asn Cys Ile Cys Asp Ile
                180                 185                 190

Asp His Cys Ser Asn Met Ala Pro Leu Tyr Ser Asp Ser Tyr Leu Val
                195                 200                 205

Phe Trp Ala Ile Phe Asn Leu Val Thr Phe Val Val Met Val Val Leu
210                 215                 220

Tyr Ala His Ile Phe Gly Tyr Val Arg Gln Arg Thr Met Arg Met Ser
225                 230                 235                 240

Arg His Ser Ser Gly Pro Arg Arg Asn Arg Asp Thr Met Met Ser Leu
                245                 250                 255

Leu Lys Thr Val Val Ile Val Leu Gly Ala Phe Ile Val Cys Trp Thr
                260                 265                 270

Pro Gly Leu Val Leu Leu Leu Asp Val Cys Cys Pro Gln Cys Asp
                275                 280                 285

Val Leu Ala Tyr Glu Lys Phe Phe Leu Leu Leu Ala Glu Phe Asn Ser
290                 295                 300

Ala Met Asn Pro Ile Ile Tyr Ser Tyr Arg Asp Lys Glu Met Ser Ala
305                 310                 315                 320

Thr Phe Arg Gln Ile Leu Cys Cys Gln Arg Asn Glu Asn Pro Asn Gly
                325                 330                 335

Pro Thr Glu Gly Ser Asp Arg Ser Ala Ser Ser Leu Asn His Thr Ile
                340                 345                 350

Leu Ala Gly Val His Ser Asn Asp His Ser Val Val
                355                 360
```

<210> SEQ ID NO 5
<211> LENGTH: 20
<212> TYPE: DNA
<213> ORGANISM: Artificial Sequence
<220> FEATURE:

-continued

<223> OTHER INFORMATION: antisense DNA

<400> SEQUENCE: 5
agctgccatg acagtgctgt                                                    20

<210> SEQ ID NO 6
<211> LENGTH: 20
<212> TYPE: DNA
<213> ORGANISM: Artificial Sequence
<220> FEATURE:
<223> OTHER INFORMATION: missense DNA

<400> SEQUENCE: 6
agcagcgttg tcactgcagt                                                    20

<210> SEQ ID NO 7
<211> LENGTH: 20
<212> TYPE: DNA
<213> ORGANISM: Artificial Sequence
<220> FEATURE:
<223> OTHER INFORMATION: antisense DNA

<400> SEQUENCE: 7
tactacaacg agaccatcgg                                                    20

<210> SEQ ID NO 8
<211> LENGTH: 20
<212> TYPE: DNA
<213> ORGANISM: Artificial Sequence
<220> FEATURE:
<223> OTHER INFORMATION: missense DNA

<400> SEQUENCE: 8
cgatacacta gaacgctcga                                                    20

<210> SEQ ID NO 9
<211> LENGTH: 3276
<212> TYPE: DNA
<213> ORGANISM: Homo sapiens
<220> FEATURE:
<221> NAME/KEY: CDS
<222> LOCATION: (87)..(2834)

<400> SEQUENCE: 9
aatagactaa acccagagcc tcaaagcagt gcactccgtg aaggcaaaga gaacacgctg        60
caaaaggctt tccaagaatc ctcgac atg gca agg agg agc tcg ttc cag tcg       113
                             Met Ala Arg Arg Ser Ser Phe Gln Ser
                              1               5 tgt cag ata ata tcc ctg ttc act ttt gcc gtt gga gtc aat atc tgc        161
Cys Gln Ile Ile Ser Leu Phe Thr Phe Ala Val Gly Val Asn Ile Cys
 10              15                  20                  25 tta gga ttc act gca cat cga att aag aga gca gaa gga tgg gag gaa        209
Leu Gly Phe Thr Ala His Arg Ile Lys Arg Ala Glu Gly Trp Glu Glu
             30                  35                  40 ggt cct cct aca gtg cta tca gac tcc ccc tgg acc aac atc tcc gga        257
Gly Pro Pro Thr Val Leu Ser Asp Ser Pro Trp Thr Asn Ile Ser Gly
         45                  50                  55 tct tgc aag ggc agg tgc ttt gaa ctt caa gag gct gga cct cct gat        305
Ser Cys Lys Gly Arg Cys Phe Glu Leu Gln Glu Ala Gly Pro Pro Asp
     60                  65                  70 tgt cgc tgt gac aac ttg tgt aag agc tat acc agt tgc tgc cat gac        353
Cys Arg Cys Asp Asn Leu Cys Lys Ser Tyr Thr Ser Cys Cys His Asp
 75                  80                  85

| | | |
|---|---|---|
| ttt gat gag ctg tgt ttg aag aca gcc cgt ggc tgg gag tgt act aag<br>Phe Asp Glu Leu Cys Leu Lys Thr Ala Arg Gly Trp Glu Cys Thr Lys<br>90               95                    100               105 | 401 | |
| gac aga tgt gga gaa gtc aga aat gaa gaa aat gcc tgt cac tgc tca<br>Asp Arg Cys Gly Glu Val Arg Asn Glu Glu Asn Ala Cys His Cys Ser<br>            110                    115                 120 | 449 | |
| gag gac tgc ttg gcc agg gga gac tgc tgt acc aat tac caa gtg gtt<br>Glu Asp Cys Leu Ala Arg Gly Asp Cys Cys Thr Asn Tyr Gln Val Val<br>                 125                  130               135 | 497 | |
| tgc aaa gga gag tcg cat tgg gtt gat gat gac tgt gag gaa ata aag<br>Cys Lys Gly Glu Ser His Trp Val Asp Asp Asp Cys Glu Glu Ile Lys<br>140                    145                    150 | 545 | |
| gcc gca gaa tgc cct gca ggg ttt gtt cgc cct cca tta atc atc ttc<br>Ala Ala Glu Cys Pro Ala Gly Phe Val Arg Pro Pro Leu Ile Ile Phe<br>      155                  160                    165 | 593 | |
| tcc gtg gat ggc ttc cgt gca tca tac atg aag aaa ggc agc aaa gtc<br>Ser Val Asp Gly Phe Arg Ala Ser Tyr Met Lys Lys Gly Ser Lys Val<br>170                    175                    180               185 | 641 | |
| atg cct aat att gaa aaa cta agg tct tgt ggc aca cac tct ccc tac<br>Met Pro Asn Ile Glu Lys Leu Arg Ser Cys Gly Thr His Ser Pro Tyr<br>                    190                    195               200 | 689 | |
| atg agg ccg gtg tac cca act aaa acc ttt cct aac tta tac act ttg<br>Met Arg Pro Val Tyr Pro Thr Lys Thr Phe Pro Asn Leu Tyr Thr Leu<br>             205                    210                    215 | 737 | |
| gcc act ggg cta tat cca gaa tca cat gga att gtt ggc aat tca atg<br>Ala Thr Gly Leu Tyr Pro Glu Ser His Gly Ile Val Gly Asn Ser Met<br>220                    225                    230 | 785 | |
| tat gat cct gta ttt gat gcc act ttt cat ctg cga ggg cga gag aaa<br>Tyr Asp Pro Val Phe Asp Ala Thr Phe His Leu Arg Gly Arg Glu Lys<br>      235                  240                    245 | 833 | |
| ttt aat cat aga tgg tgg gga ggt caa ccg cta tgg att aca gcc acc<br>Phe Asn His Arg Trp Trp Gly Gly Gln Pro Leu Trp Ile Thr Ala Thr<br>250                    255                    260               265 | 881 | |
| aag caa ggg gtg aaa gct gga aca ttc ttt tgg tct gtt gtc atc cct<br>Lys Gln Gly Val Lys Ala Gly Thr Phe Phe Trp Ser Val Val Ile Pro<br>                    270                    275               280 | 929 | |
| cac gag cgg aga ata tta acc ata ttg cag tgg ctc acc ctg cca gat<br>His Glu Arg Arg Ile Leu Thr Ile Leu Gln Trp Leu Thr Leu Pro Asp<br>                        285                    290               295 | 977 | |
| cat gag agg cct tcg gtc tat gcc ttc tat tct gag caa cct gat ttc<br>His Glu Arg Pro Ser Val Tyr Ala Phe Tyr Ser Glu Gln Pro Asp Phe<br>                      300                    305               310 | 1025 | |
| tct gga cac aaa tat ggc cct ttc ggc cct gag gag agt agt tat ggc<br>Ser Gly His Lys Tyr Gly Pro Phe Gly Pro Glu Glu Ser Ser Tyr Gly<br>315                    320                    325 | 1073 | |
| tca cct ttt act ccg gct aag aga cct aag agg aaa gtt gcc cct aag<br>Ser Pro Phe Thr Pro Ala Lys Arg Pro Lys Arg Lys Val Ala Pro Lys<br>330                    335                    340               345 | 1121 | |
| agg aga cag gaa aga cca gtt gct cct cca aag aaa aga aga aaa<br>Arg Arg Gln Glu Arg Pro Val Ala Pro Pro Lys Lys Arg Arg Arg Lys<br>                    350                    355               360 | 1169 | |
| ata cat agg atg gat cat tat gct gcg gaa act cgt cag gac aaa atg<br>Ile His Arg Met Asp His Tyr Ala Ala Glu Thr Arg Gln Asp Lys Met<br>                   365                    370               375 | 1217 | |
| aca aat cct ctg agg gaa atc gac aaa att gtg ggg caa tta atg gat<br>Thr Asn Pro Leu Arg Glu Ile Asp Lys Ile Val Gly Gln Leu Met Asp<br>                380                   385                390 | 1265 | |
| gga ctg aaa caa cta aaa ctg cat cgg tgt gtc aac gtc atc ttt gtc<br>Gly Leu Lys Gln Leu Lys Leu His Arg Cys Val Asn Val Ile Phe Val<br>395                    400                    405 | 1313 | |

```
gga gac cat gga atg gaa gat gtc aca tgt gat aga act gag ttc ttg    1361
Gly Asp His Gly Met Glu Asp Val Thr Cys Asp Arg Thr Glu Phe Leu
410             415                 420                 425 agt aat tac cta act aat gtg gat gat att act tta gtg cct gga act    1409
Ser Asn Tyr Leu Thr Asn Val Asp Asp Ile Thr Leu Val Pro Gly Thr
            430                 435                 440 cta gga aga att cga tcc aaa ttt agc aac aat gct aaa tat gac ccc    1457
Leu Gly Arg Ile Arg Ser Lys Phe Ser Asn Asn Ala Lys Tyr Asp Pro
                445                 450                 455 aaa gcc att att gcc aat ctc acg tgt aaa aaa cca gat cag cac ttt    1505
Lys Ala Ile Ile Ala Asn Leu Thr Cys Lys Lys Pro Asp Gln His Phe
        460                 465                 470 aag cct tac ttg aaa cag cac ctt ccc aaa cgt ttg cac tat gcc aac    1553
Lys Pro Tyr Leu Lys Gln His Leu Pro Lys Arg Leu His Tyr Ala Asn
    475                 480                 485 aac aga aga att gag gat atc cat tta ttg gtg gaa cgc aga tgg cat    1601
Asn Arg Arg Ile Glu Asp Ile His Leu Leu Val Glu Arg Arg Trp His
490                 495                 500                 505 gtt gca agg aaa cct ttg gat gtt tat aag aaa cca tca gga aaa tgc    1649
Val Ala Arg Lys Pro Leu Asp Val Tyr Lys Lys Pro Ser Gly Lys Cys
                510                 515                 520 ttt ttc cag gga gac cac gga ttt gat aac aag gtc aac agc atg cag    1697
Phe Phe Gln Gly Asp His Gly Phe Asp Asn Lys Val Asn Ser Met Gln
        525                 530                 535 act gtt ttt gta ggt tat ggc tca aca ttt aag tac aag act aaa gtg    1745
Thr Val Phe Val Gly Tyr Gly Ser Thr Phe Lys Tyr Lys Thr Lys Val
    540                 545                 550 cct cca ttt gaa aac att gaa ctt tac aat gtt atg tgt gat ctc ctg    1793
Pro Pro Phe Glu Asn Ile Glu Leu Tyr Asn Val Met Cys Asp Leu Leu
555                 560                 565 gga ttg aag cca gct cct aat aat ggg acc cat gga agt ttg aat cat    1841
Gly Leu Lys Pro Ala Pro Asn Asn Gly Thr His Gly Ser Leu Asn His
570                 575                 580                 585 ctc ctg cgc act aat acc ttc agg cca acc atg cca gag gaa gtt acc    1889
Leu Leu Arg Thr Asn Thr Phe Arg Pro Thr Met Pro Glu Glu Val Thr
                590                 595                 600 aga ccc aat tat cca ggg att atg tac ctt cag tct gat ttt gac ctg    1937
Arg Pro Asn Tyr Pro Gly Ile Met Tyr Leu Gln Ser Asp Phe Asp Leu
            605                 610                 615 ggc tgc act tgt gat gat aag gta gag cca aag aac aag ttg gat gaa    1985
Gly Cys Thr Cys Asp Asp Lys Val Glu Pro Lys Asn Lys Leu Asp Glu
        620                 625                 630 ctc aac aaa cgg ctt cat aca aaa ggg tct aca gaa gag aga cac ctc    2033
Leu Asn Lys Arg Leu His Thr Lys Gly Ser Thr Glu Glu Arg His Leu
    635                 640                 645 ctc tat ggg cga cct gca gtg ctt tat cgg act aga tat gat atc tta    2081
Leu Tyr Gly Arg Pro Ala Val Leu Tyr Arg Thr Arg Tyr Asp Ile Leu
650                 655                 660                 665 tat cac act gac ttt gaa agt ggt tat agt gaa ata ttc cta atg cca    2129
Tyr His Thr Asp Phe Glu Ser Gly Tyr Ser Glu Ile Phe Leu Met Pro
                670                 675                 680 ctc tgg aca tca tat act gtt tcc aaa cag gct gag gtt tcc agc gtt    2177
Leu Trp Thr Ser Tyr Thr Val Ser Lys Gln Ala Glu Val Ser Ser Val
            685                 690                 695 cct gac cat ctg acc agt tgc gtc cgg cct gat gtc cgt gtt tct ccg    2225
Pro Asp His Leu Thr Ser Cys Val Arg Pro Asp Val Arg Val Ser Pro
        700                 705                 710 agt ttc agt cag aac tgt ttg gcc tac aaa aat gat aag cag atg tcc    2273
Ser Phe Ser Gln Asn Cys Leu Ala Tyr Lys Asn Asp Lys Gln Met Ser
```

| | | | | | | | | | | | | | | | | |
|---|---|---|---|---|---|---|---|---|---|---|---|---|---|---|---|---|
| | | 715 | | | | | 720 | | | | | | 725 | | | |
| tac | gga | ttc | ctc | ttt | cct | cct | tat | ctg | agc | tct | tca | cca | gag | gct | aaa | 2321 |
| Tyr | Gly | Phe | Leu | Phe | Pro | Pro | Tyr | Leu | Ser | Ser | Ser | Pro | Glu | Ala | Lys | |
| 730 | | | | | 735 | | | | | 740 | | | | | 745 | |
| tat | gat | gca | ttc | ctt | gta | acc | aat | atg | gtt | cca | atg | tat | cct | gct | ttc | 2369 |
| Tyr | Asp | Ala | Phe | Leu | Val | Thr | Asn | Met | Val | Pro | Met | Tyr | Pro | Ala | Phe | |
| | | | | 750 | | | | | 755 | | | | | 760 | | |
| aaa | cgg | gtc | tgg | aat | tat | ttc | caa | agg | gta | ttg | gtg | aag | aaa | tat | gct | 2417 |
| Lys | Arg | Val | Trp | Asn | Tyr | Phe | Gln | Arg | Val | Leu | Val | Lys | Lys | Tyr | Ala | |
| | | 765 | | | | | 770 | | | | | 775 | | | | |
| tcg | gaa | aga | aat | gga | gtt | aac | gtg | ata | agt | gga | cca | atc | ttc | gac | tat | 2465 |
| Ser | Glu | Arg | Asn | Gly | Val | Asn | Val | Ile | Ser | Gly | Pro | Ile | Phe | Asp | Tyr | |
| | | | 780 | | | | | 785 | | | | | 790 | | | |
| gac | tat | gat | ggc | tta | cat | gac | aca | gaa | gac | aaa | ata | aaa | cag | tac | gtg | 2513 |
| Asp | Tyr | Asp | Gly | Leu | His | Asp | Thr | Glu | Asp | Lys | Ile | Lys | Gln | Tyr | Val | |
| 795 | | | | | 800 | | | | | 805 | | | | | | |
| gaa | ggc | agt | tcc | att | cct | gtt | cca | act | cac | tac | tac | agc | atc | atc | acc | 2561 |
| Glu | Gly | Ser | Ser | Ile | Pro | Val | Pro | Thr | His | Tyr | Tyr | Ser | Ile | Ile | Thr | |
| 810 | | | | | 815 | | | | | 820 | | | | | 825 | |
| agc | tgt | ctg | gat | ttc | act | cag | cct | gcc | gac | aag | tgt | gac | ggc | cct | ctc | 2609 |
| Ser | Cys | Leu | Asp | Phe | Thr | Gln | Pro | Ala | Asp | Lys | Cys | Asp | Gly | Pro | Leu | |
| | | | | | 830 | | | | | 835 | | | | | 840 | |
| tct | gtg | tcc | tcc | ttc | atc | ctg | cct | cac | cgg | cct | gac | aac | gag | gag | agc | 2657 |
| Ser | Val | Ser | Ser | Phe | Ile | Leu | Pro | His | Arg | Pro | Asp | Asn | Glu | Glu | Ser | |
| | | | 845 | | | | | 850 | | | | | 855 | | | |
| tgc | aat | agc | tca | gag | gac | gaa | tca | aaa | tgg | gta | gaa | gaa | ctc | atg | aag | 2705 |
| Cys | Asn | Ser | Ser | Glu | Asp | Glu | Ser | Lys | Trp | Val | Glu | Glu | Leu | Met | Lys | |
| | | 860 | | | | | 865 | | | | | 870 | | | | |
| atg | cac | aca | gct | agg | gtg | cgt | gac | att | gaa | cat | ctc | acc | agc | ctg | gac | 2753 |
| Met | His | Thr | Ala | Arg | Val | Arg | Asp | Ile | Glu | His | Leu | Thr | Ser | Leu | Asp | |
| 875 | | | | | 880 | | | | | 885 | | | | | | |
| ttc | ttc | cga | aag | acc | agc | cgc | agc | tac | cca | gaa | atc | ctg | aca | ctc | aag | 2801 |
| Phe | Phe | Arg | Lys | Thr | Ser | Arg | Ser | Tyr | Pro | Glu | Ile | Leu | Thr | Leu | Lys | |
| 890 | | | | | 895 | | | | | 900 | | | | | 905 | |
| aca | tac | ctg | cat | aca | tat | gag | agc | gag | att | taa | ctttctgagc | | | atctgcagta | | 2854 |
| Thr | Tyr | Leu | His | Thr | Tyr | Glu | Ser | Glu | Ile | | | | | | | |
| | | | | 910 | | | | | 915 | | | | | | | | cagtcttatc aactggttgt atattttat attgttttg tatttattaa tttgaaacca   2914 ggacattaaa aatgttagta ttttaatcct gtaccaaatc tgacatatta tgcctgaatg   2974 actccactgt ttttctctaa tgcttgattt aggtagcctt gtgttctgag tagagcttgt   3034 aataaatact gcagcttgag tttttagtgg aagcttctaa atggtgctgc agatttgata   3094 tttgcattga ggaaatatta attttccaat gcacagttgc cacatttagt cctgtactgt   3154 atggaaacac tgattttgta aagttgcctt tatttgctgt taactgttaa ctatgacaga   3214 tatatttaag cctataaaac caatcttaaa cataataaat cacacattca gtttttctg   3274 gt                                                                  3276

<210> SEQ ID NO 10
<211> LENGTH: 915
<212> TYPE: PRT
<213> ORGANISM: Homo sapiens

<400> SEQUENCE: 10

Met Ala Arg Arg Ser Ser Phe Gln Ser Cys Gln Ile Ile Ser Leu Phe
1               5                   10                  15

Thr Phe Ala Val Gly Val Asn Ile Cys Leu Gly Phe Thr Ala His Arg
            20                  25                  30

```
Ile Lys Arg Ala Glu Gly Trp Glu Gly Pro Pro Thr Val Leu Ser
    35              40              45

Asp Ser Pro Trp Thr Asn Ile Ser Gly Ser Cys Lys Gly Arg Cys Phe
    50              55              60

Glu Leu Gln Glu Ala Gly Pro Pro Asp Cys Arg Cys Asp Asn Leu Cys
65              70              75              80

Lys Ser Tyr Thr Ser Cys Cys His Asp Phe Asp Glu Leu Cys Leu Lys
                85              90              95

Thr Ala Arg Gly Trp Glu Cys Thr Lys Asp Arg Cys Gly Glu Val Arg
            100             105             110

Asn Glu Glu Asn Ala Cys His Cys Ser Glu Asp Cys Leu Ala Arg Gly
                115             120             125

Asp Cys Cys Thr Asn Tyr Gln Val Val Cys Lys Gly Glu Ser His Trp
    130             135             140

Val Asp Asp Asp Cys Glu Glu Ile Lys Ala Ala Glu Cys Pro Ala Gly
145             150             155             160

Phe Val Arg Pro Pro Leu Ile Ile Phe Ser Val Asp Gly Phe Arg Ala
                165             170             175

Ser Tyr Met Lys Lys Gly Ser Lys Val Met Pro Asn Ile Glu Lys Leu
        180             185             190

Arg Ser Cys Gly Thr His Ser Pro Tyr Met Arg Pro Val Tyr Pro Thr
        195             200             205

Lys Thr Phe Pro Asn Leu Tyr Thr Leu Ala Thr Gly Leu Tyr Pro Glu
    210             215             220

Ser His Gly Ile Val Gly Asn Ser Met Tyr Asp Pro Val Phe Asp Ala
225             230             235             240

Thr Phe His Leu Arg Gly Arg Glu Lys Phe Asn His Arg Trp Trp Gly
                245             250             255

Gly Gln Pro Leu Trp Ile Thr Ala Thr Lys Gln Gly Val Lys Ala Gly
            260             265             270

Thr Phe Phe Trp Ser Val Val Ile Pro His Glu Arg Arg Ile Leu Thr
    275             280             285

Ile Leu Gln Trp Leu Thr Leu Pro Asp His Glu Arg Pro Ser Val Tyr
    290             295             300

Ala Phe Tyr Ser Glu Gln Pro Asp Phe Ser Gly His Lys Tyr Gly Pro
305             310             315             320

Phe Gly Pro Glu Glu Ser Ser Tyr Gly Ser Pro Phe Thr Pro Ala Lys
                325             330             335

Arg Pro Lys Arg Lys Val Ala Pro Lys Arg Arg Gln Glu Arg Pro Val
            340             345             350

Ala Pro Pro Lys Lys Arg Arg Lys Ile His Arg Met Asp His Tyr
                355             360             365

Ala Ala Glu Thr Arg Gln Asp Lys Met Thr Asn Pro Leu Arg Glu Ile
    370             375             380

Asp Lys Ile Val Gly Gln Leu Met Asp Gly Leu Lys Gln Leu Lys Leu
385             390             395             400

His Arg Cys Val Asn Val Ile Phe Val Gly Asp His Gly Met Glu Asp
                405             410             415

Val Thr Cys Asp Arg Thr Glu Phe Leu Ser Asn Tyr Leu Thr Asn Val
            420             425             430

Asp Asp Ile Thr Leu Val Pro Gly Thr Leu Gly Arg Ile Arg Ser Lys
            435             440             445
```

```
Phe Ser Asn Asn Ala Lys Tyr Asp Pro Lys Ala Ile Ile Ala Asn Leu
    450                 455                 460

Thr Cys Lys Lys Pro Asp Gln His Phe Lys Pro Tyr Leu Lys Gln His
465                 470                 475                 480

Leu Pro Lys Arg Leu His Tyr Ala Asn Asn Arg Arg Ile Glu Asp Ile
                485                 490                 495

His Leu Leu Val Glu Arg Arg Trp His Val Ala Arg Lys Pro Leu Asp
                500                 505                 510

Val Tyr Lys Lys Pro Ser Gly Lys Cys Phe Phe Gln Gly Asp His Gly
                515                 520                 525

Phe Asp Asn Lys Val Asn Ser Met Gln Thr Val Phe Val Gly Tyr Gly
530                 535                 540

Ser Thr Phe Lys Tyr Lys Thr Lys Val Pro Pro Phe Glu Asn Ile Glu
545                 550                 555                 560

Leu Tyr Asn Val Met Cys Asp Leu Leu Gly Leu Lys Pro Ala Pro Asn
                565                 570                 575

Asn Gly Thr His Gly Ser Leu Asn His Leu Leu Arg Thr Asn Thr Phe
                580                 585                 590

Arg Pro Thr Met Pro Glu Glu Val Thr Arg Pro Asn Tyr Pro Gly Ile
                595                 600                 605

Met Tyr Leu Gln Ser Asp Phe Asp Leu Gly Cys Thr Cys Asp Asp Lys
    610                 615                 620

Val Glu Pro Lys Asn Lys Leu Asp Glu Leu Asn Lys Arg Leu His Thr
625                 630                 635                 640

Lys Gly Ser Thr Glu Glu Arg His Leu Leu Tyr Gly Arg Pro Ala Val
                645                 650                 655

Leu Tyr Arg Thr Arg Tyr Asp Ile Leu Tyr His Thr Asp Phe Glu Ser
                660                 665                 670

Gly Tyr Ser Glu Ile Phe Leu Met Pro Leu Trp Thr Ser Tyr Thr Val
            675                 680                 685

Ser Lys Gln Ala Glu Val Ser Ser Val Pro Asp His Leu Thr Ser Cys
    690                 695                 700

Val Arg Pro Asp Val Arg Val Ser Pro Ser Phe Ser Gln Asn Cys Leu
705                 710                 715                 720

Ala Tyr Lys Asn Asp Lys Gln Met Ser Tyr Gly Phe Leu Phe Pro Pro
                725                 730                 735

Tyr Leu Ser Ser Ser Pro Glu Ala Lys Tyr Asp Ala Phe Leu Val Thr
                740                 745                 750

Asn Met Val Pro Met Tyr Pro Ala Phe Lys Arg Val Trp Asn Tyr Phe
        755                 760                 765

Gln Arg Val Leu Val Lys Lys Tyr Ala Ser Glu Arg Asn Gly Val Asn
    770                 775                 780

Val Ile Ser Gly Pro Ile Phe Asp Tyr Asp Tyr Asp Gly Leu His Asp
785                 790                 795                 800

Thr Glu Asp Lys Ile Lys Gln Tyr Val Glu Gly Ser Ser Ile Pro Val
                805                 810                 815

Pro Thr His Tyr Tyr Ser Ile Ile Thr Ser Cys Leu Asp Phe Thr Gln
                820                 825                 830

Pro Ala Asp Lys Cys Asp Gly Pro Leu Ser Val Ser Ser Phe Ile Leu
                835                 840                 845

Pro His Arg Pro Asp Asn Glu Glu Ser Cys Asn Ser Ser Glu Asp Glu
            850                 855                 860

Ser Lys Trp Val Glu Glu Leu Met Lys Met His Thr Ala Arg Val Arg
```

```
                865                 870                 875                 880
Asp Ile Glu His Leu Thr Ser Leu Asp Phe Phe Arg Lys Thr Ser Arg
                    885                 890                 895
Ser Tyr Pro Glu Ile Leu Thr Leu Lys Thr Tyr Leu His Thr Tyr Glu
            900                 905                 910
Ser Glu Ile
        915

<210> SEQ ID NO 11
<211> LENGTH: 3124
<212> TYPE: DNA
<213> ORGANISM: Mus musculus
<220> FEATURE:
<221> NAME/KEY: CDS
<222> LOCATION: (42)..(2630)

<400> SEQUENCE: 11
gcagagaaca ccctgcagag gttttccaag aatccctcgg c atg gca aga caa ggc       56
                                             Met Ala Arg Gln Gly
                                              1               5 tgt ttc ggg tca tac cag gta ata tcc ttg ttc act ttt gcc atc ggc       104
Cys Phe Gly Ser Tyr Gln Val Ile Ser Leu Phe Thr Phe Ala Ile Gly
             10                  15                  20 gtc aat ctc tgc tta gga ttc aca gca agt cga att aag agg gcc gaa       152
Val Asn Leu Cys Leu Gly Phe Thr Ala Ser Arg Ile Lys Arg Ala Glu
         25                  30                  35 tgg gat gaa gga cct ccc aca gtg tta tct gac tct cca tgg acc aac       200
Trp Asp Glu Gly Pro Pro Thr Val Leu Ser Asp Ser Pro Trp Thr Asn
     40                  45                  50 aca tct gga tcc tgc aaa ggt aga tgc ttt gag ctt caa gag gtt gga       248
Thr Ser Gly Ser Cys Lys Gly Arg Cys Phe Glu Leu Gln Glu Val Gly
 55                  60                  65 cct cct gac tgt cgg tgt gac aac cta tgt aag agc tac agc agc tgc       296
Pro Pro Asp Cys Arg Cys Asp Asn Leu Cys Lys Ser Tyr Ser Ser Cys
 70                  75                  80                  85 tgc cat gat ttt gat gag ctc tgt ttg aaa aca gct cga ggc tgg gag       344
Cys His Asp Phe Asp Glu Leu Cys Leu Lys Thr Ala Arg Gly Trp Glu
             90                  95                 100 tgc acc aaa gac aga tgt ggg gaa gta cga aat gag gaa aat gcc tgt       392
Cys Thr Lys Asp Arg Cys Gly Glu Val Arg Asn Glu Glu Asn Ala Cys
        105                 110                 115 cac tgc tca gaa gac tgc ttg tcc cgg gga gac tgc tgt acc aac tac       440
His Cys Ser Glu Asp Cys Leu Ser Arg Gly Asp Cys Cys Thr Asn Tyr
    120                 125                 130 caa gtg gtc tgc aaa gga gaa tca cac tgg gta gat gat gac tgt gaa       488
Gln Val Val Cys Lys Gly Glu Ser His Trp Val Asp Asp Asp Cys Glu
135                 140                 145 gaa ata aga gtc ccc gaa tgc cct gca ggg ttt gtc cgc cct ccg tta       536
Glu Ile Arg Val Pro Glu Cys Pro Ala Gly Phe Val Arg Pro Pro Leu
150                 155                 160                 165 atc atc ttc tct gtg gat gga ttc cgt gca tcg tac atg aag aaa ggc       584
Ile Ile Phe Ser Val Asp Gly Phe Arg Ala Ser Tyr Met Lys Lys Gly
                170                 175                 180 agc aag gtt atg ccc aac att gag aaa ctg cgg tcc tgt ggc acc cat       632
Ser Lys Val Met Pro Asn Ile Glu Lys Leu Arg Ser Cys Gly Thr His
            185                 190                 195 gct ccc tac atg agg cct gta tac cct aca aaa acc ttc cct aat ctg       680
Ala Pro Tyr Met Arg Pro Val Tyr Pro Thr Lys Thr Phe Pro Asn Leu
        200                 205                 210 tat acg ctg gcc act ggt tta tat cca gaa tcc atg gga atc gtt ggc       728
```

```
Tyr Thr Leu Ala Thr Gly Leu Tyr Pro Glu Ser His Gly Ile Val Gly
    215             220                 225 aat tca atg tat gac cct gtc ttt gat gct act ttc cat ctt cga ggg       776
Asn Ser Met Tyr Asp Pro Val Phe Asp Ala Thr Phe His Leu Arg Gly
230                 235                 240                 245 cga gag aag ttt aac cat aga tgg tgg gga ggc caa ccg cta tgg att       824
Arg Glu Lys Phe Asn His Arg Trp Trp Gly Gly Gln Pro Leu Trp Ile
                250                 255                 260 aca gcc acc aag caa ggg gtg aga gcc ggg aca ttc ttt tgg tct gtg       872
Thr Ala Thr Lys Gln Gly Val Arg Ala Gly Thr Phe Phe Trp Ser Val
            265                 270                 275 agc atc cct cac gag cgg aga atc cta act atc ctt cag tgg ctt tcc       920
Ser Ile Pro His Glu Arg Arg Ile Leu Thr Ile Leu Gln Trp Leu Ser
        280                 285                 290 ctg cca gac aat gag agg cct tca gtt tat gcc ttc tac tcc gag cag       968
Leu Pro Asp Asn Glu Arg Pro Ser Val Tyr Ala Phe Tyr Ser Glu Gln
    295                 300                 305 cct gat ttt tct gga cac aag tac ggc cct ttt ggc cct gag atg aca      1016
Pro Asp Phe Ser Gly His Lys Tyr Gly Pro Phe Gly Pro Glu Met Thr
310                 315                 320                 325 aat cct ctg agg gag att gac aag acc gtg ggg cag tta atg gac gga      1064
Asn Pro Leu Arg Glu Ile Asp Lys Thr Val Gly Gln Leu Met Asp Gly
                330                 335                 340 ctg aaa caa ctc aag ctg cac cgt tgt gtg aat gtt atc ttt gtt gga      1112
Leu Lys Gln Leu Lys Leu His Arg Cys Val Asn Val Ile Phe Val Gly
            345                 350                 355 gac cat gga atg gaa gac gtg aca tgt gac aga act gag ttc ttg agc      1160
Asp His Gly Met Glu Asp Val Thr Cys Asp Arg Thr Glu Phe Leu Ser
        360                 365                 370 aac tat ctg act aac gtg gat gat att act tta gta cct gga act cta      1208
Asn Tyr Leu Thr Asn Val Asp Asp Ile Thr Leu Val Pro Gly Thr Leu
    375                 380                 385 gga aga att cga ccc aag att ccc aat aat ctt aaa tat gac cct aaa      1256
Gly Arg Ile Arg Pro Lys Ile Pro Asn Asn Leu Lys Tyr Asp Pro Lys
390                 395                 400                 405 gcc att att gct aac ctc acg tgt aaa aaa cca gat cag cac ttt aag      1304
Ala Ile Ile Ala Asn Leu Thr Cys Lys Lys Pro Asp Gln His Phe Lys
                410                 415                 420 cct tac atg aaa cag cac ctt ccc aaa cgt ttg cac tat gcc aac aat      1352
Pro Tyr Met Lys Gln His Leu Pro Lys Arg Leu His Tyr Ala Asn Asn
            425                 430                 435 cgg aga atc gag gat ctc cat tta ttg gtg gaa cgc aga tgg cat gtt      1400
Arg Arg Ile Glu Asp Leu His Leu Leu Val Glu Arg Arg Trp His Val
        440                 445                 450 gca agg aaa cct ttg gac gtt tat aag aag ccg tca gga aaa tgt ttt      1448
Ala Arg Lys Pro Leu Asp Val Tyr Lys Lys Pro Ser Gly Lys Cys Phe
    455                 460                 465 ttc cag ggt gac cac ggc ttt gat aac aag gtc aat agc atg cag act      1496
Phe Gln Gly Asp His Gly Phe Asp Asn Lys Val Asn Ser Met Gln Thr
470                 475                 480                 485 gtt ttt gta ggt tat ggc cca act ttt aag tac agg act aaa gtg cct      1544
Val Phe Val Gly Tyr Gly Pro Thr Phe Lys Tyr Arg Thr Lys Val Pro
                490                 495                 500 cca ttt gaa aac att gaa ctt tat aat gtt atg tgc gat ctc cta agc      1592
Pro Phe Glu Asn Ile Glu Leu Tyr Asn Val Met Cys Asp Leu Leu Ser
            505                 510                 515 ttg aag cca gct ccc aat aat gga aca cat gga agt ttg aat cac ctg      1640
Leu Lys Pro Ala Pro Asn Asn Gly Thr His Gly Ser Leu Asn His Leu
        520                 525                 530
```

-continued

| | | |
|---|---|---|
| cta cgc aca aat acc ttt agg cca acc cta cca gag gaa gtc agc aga<br>Leu Arg Thr Asn Thr Phe Arg Pro Thr Leu Pro Glu Glu Val Ser Arg<br>535 540 545 | 1688 | |
| acc aat tac cca ggg att atg tac ctt cag tct gat ttt gac ctg ggc<br>Thr Asn Tyr Pro Gly Ile Met Tyr Leu Gln Ser Asp Phe Asp Leu Gly<br>550 555 560 565 | 1736 | |
| tgc acc tgt gat gat aag gta aag cca aag aac aaa ttg gaa gaa cta<br>Cys Thr Cys Asp Asp Lys Val Lys Pro Lys Asn Lys Leu Glu Glu Leu<br>570 575 580 | 1784 | |
| aat aaa cgc ctt cat acc aaa gga tct aca gaa gag aga cat ctc ctg<br>Asn Lys Arg Leu His Thr Lys Gly Ser Thr Glu Glu Arg His Leu Leu<br>585 590 595 | 1832 | |
| tat gga cga cct gca gtg ctt tat cgg act agc tat gat atc tta tac<br>Tyr Gly Arg Pro Ala Val Leu Tyr Arg Thr Ser Tyr Asp Ile Leu Tyr<br>600 605 610 | 1880 | |
| cat acg gac ttt gaa agt ggt tac agt gaa ata ttc tta atg cct ctc<br>His Thr Asp Phe Glu Ser Gly Tyr Ser Glu Ile Phe Leu Met Pro Leu<br>615 620 625 | 1928 | |
| tgg act tct tat acc att tct aag cag gct gag gtc tct agc atc cca<br>Trp Thr Ser Tyr Thr Ile Ser Lys Gln Ala Glu Val Ser Ser Ile Pro<br>630 635 640 645 | 1976 | |
| gag cac ctg acc aac tgt gtt cgc cct gat gtc cgt gta tct cct gga<br>Glu His Leu Thr Asn Cys Val Arg Pro Asp Val Arg Val Ser Pro Gly<br>650 655 660 | 2024 | |
| ttc agt cag aac tgt tta gcc tat aaa aat gat aaa cag atg tcc tat<br>Phe Ser Gln Asn Cys Leu Ala Tyr Lys Asn Asp Lys Gln Met Ser Tyr<br>665 670 675 | 2072 | |
| gga ttc ctt ttt cct ccc tat ctg agc tct tcc cca gaa gcg aaa tat<br>Gly Phe Leu Phe Pro Pro Tyr Leu Ser Ser Ser Pro Glu Ala Lys Tyr<br>680 685 690 | 2120 | |
| gat gca ttc ctt gta acc aac atg gtt cca atg tac cct gcc ttc aaa<br>Asp Ala Phe Leu Val Thr Asn Met Val Pro Met Tyr Pro Ala Phe Lys<br>695 700 705 | 2168 | |
| cgt gtt tgg act tat ttc caa agg gtc ttg gtg aag aaa tat gcg tca<br>Arg Val Trp Thr Tyr Phe Gln Arg Val Leu Val Lys Lys Tyr Ala Ser<br>710 715 720 725 | 2216 | |
| gaa agg aat ggg gtc aac gta ata agt gga ccg atc ttt gac tac aat<br>Glu Arg Asn Gly Val Asn Val Ile Ser Gly Pro Ile Phe Asp Tyr Asn<br>730 735 740 | 2264 | |
| tac aat ggc tta cgt gac att gag gat gaa att aaa cag tat gtg gaa<br>Tyr Asn Gly Leu Arg Asp Ile Glu Asp Glu Ile Lys Gln Tyr Val Glu<br>745 750 755 | 2312 | |
| ggc agc tct att cct gtc cct acc cac tac tac agc atc atc acc agc<br>Gly Ser Ser Ile Pro Val Pro Thr His Tyr Tyr Ser Ile Ile Thr Ser<br>760 765 770 | 2360 | |
| tgc ctg gac ttc act cag cct gca gac aag tgt gat ggt cct ctc tct<br>Cys Leu Asp Phe Thr Gln Pro Ala Asp Lys Cys Asp Gly Pro Leu Ser<br>775 780 785 | 2408 | |
| gtg tct tct ttc atc ctt cct cac cga cct gac aat gat gag agc tgt<br>Val Ser Ser Phe Ile Leu Pro His Arg Pro Asp Asn Asp Glu Ser Cys<br>790 795 800 805 | 2456 | |
| aat agt tcc gag gat gag tcg aag tgg gta gag gaa ctc atg aag atg<br>Asn Ser Ser Glu Asp Glu Ser Lys Trp Val Glu Glu Leu Met Lys Met<br>810 815 820 | 2504 | |
| cac aca gct cgg gtg agg gac atc gag cat ctc acc ggt ttg gat ttc<br>His Thr Ala Arg Val Arg Asp Ile Glu His Leu Thr Gly Leu Asp Phe<br>825 830 835 | 2552 | |
| tac cgg aag act agc cgt agc tat tcg gaa att ctg acc ctc aag aca<br>Tyr Arg Lys Thr Ser Arg Ser Tyr Ser Glu Ile Leu Thr Leu Lys Thr<br>840 845 850 | 2600 | |

-continued

```
tac ctg cat aca tat gag agc gag att taa cttcctgggc ctgggcagtg   2650
Tyr Leu His Thr Tyr Glu Ser Glu Ile
    855                 860 tagtcttagc aactggtgta tattttata tgggtgttat ttattaattt gaaaccagga   2710
cataaacaaa caaagaaaca aatgaaaaaa aaaaaaccac ttagtatttt aatcctgtac   2770
caaatctgac atattaagcc tgaatgactg tgctgttttt ctcctttaat tcttgatgta   2830
gacagagttg tgttctgagc agagtttata gtgaacactg aagctcgtga tccaagtaga   2890
agcttctaca tggtgctgcc agttggatat tgtgcattga ggaaatacta ggtttcccag   2950
tgcccagtca ccacgtgtag tcctgttctg tattgaaaga ctgattttgt aaaggtgcat   3010
tcatctgcgg ttaactttga cagacatatt taagccttat agaccaatct taaatataat   3070
aaatcacaca ttcagatttt tccctggaaa aaaaaaaaa aagaaaaaaa aaaa          3124
```

<210> SEQ ID NO 12
<211> LENGTH: 862
<212> TYPE: PRT
<213> ORGANISM: Mus musculus

<400> SEQUENCE: 12

```
Met Ala Arg Gln Gly Cys Phe Gly Ser Tyr Gln Val Ile Ser Leu Phe
1               5                   10                  15

Thr Phe Ala Ile Gly Val Asn Leu Cys Leu Gly Phe Thr Ala Ser Arg
            20                  25                  30

Ile Lys Arg Ala Glu Trp Asp Glu Gly Pro Pro Thr Val Leu Ser Asp
        35                  40                  45

Ser Pro Trp Thr Asn Thr Ser Gly Ser Cys Lys Gly Arg Cys Phe Glu
    50                  55                  60

Leu Gln Glu Val Gly Pro Pro Asp Cys Arg Cys Asp Asn Leu Cys Lys
65                  70                  75                  80

Ser Tyr Ser Ser Cys Cys His Asp Phe Asp Glu Leu Cys Leu Lys Thr
                85                  90                  95

Ala Arg Gly Trp Glu Cys Thr Lys Asp Arg Cys Gly Glu Val Arg Asn
            100                 105                 110

Glu Glu Asn Ala Cys His Cys Ser Glu Asp Cys Leu Ser Arg Gly Asp
        115                 120                 125

Cys Cys Thr Asn Tyr Gln Val Val Cys Lys Gly Glu Ser His Trp Val
    130                 135                 140

Asp Asp Asp Cys Glu Glu Ile Arg Val Pro Glu Cys Pro Ala Gly Phe
145                 150                 155                 160

Val Arg Pro Pro Leu Ile Ile Phe Ser Val Asp Gly Phe Arg Ala Ser
                165                 170                 175

Tyr Met Lys Lys Gly Ser Lys Val Met Pro Asn Ile Glu Lys Leu Arg
            180                 185                 190

Ser Cys Gly Thr His Ala Pro Tyr Met Arg Pro Val Tyr Pro Thr Lys
        195                 200                 205

Thr Phe Pro Asn Leu Tyr Thr Leu Ala Thr Gly Leu Tyr Pro Glu Ser
    210                 215                 220

His Gly Ile Val Gly Asn Ser Met Tyr Asp Pro Val Phe Asp Ala Thr
225                 230                 235                 240

Phe His Leu Arg Gly Arg Glu Lys Phe Asn His Arg Trp Trp Gly Gly
                245                 250                 255

Gln Pro Leu Trp Ile Thr Ala Thr Lys Gln Gly Val Arg Ala Gly Thr
            260                 265                 270
```

-continued

```
Phe Phe Trp Ser Val Ser Ile Pro His Glu Arg Arg Ile Leu Thr Ile
            275                 280                 285

Leu Gln Trp Leu Ser Leu Pro Asp Asn Glu Arg Pro Ser Val Tyr Ala
    290                 295                 300

Phe Tyr Ser Glu Gln Pro Asp Phe Ser Gly His Lys Tyr Gly Pro Phe
305                 310                 315                 320

Gly Pro Glu Met Thr Asn Pro Leu Arg Glu Ile Asp Lys Thr Val Gly
                325                 330                 335

Gln Leu Met Asp Gly Leu Lys Gln Leu Lys Leu His Arg Cys Val Asn
                340                 345                 350

Val Ile Phe Val Gly Asp His Gly Met Glu Asp Val Thr Cys Asp Arg
            355                 360                 365

Thr Glu Phe Leu Ser Asn Tyr Leu Thr Asn Val Asp Asp Ile Thr Leu
    370                 375                 380

Val Pro Gly Thr Leu Gly Arg Ile Arg Pro Lys Ile Pro Asn Asn Leu
385                 390                 395                 400

Lys Tyr Asp Pro Lys Ala Ile Ile Ala Asn Leu Thr Cys Lys Lys Pro
                405                 410                 415

Asp Gln His Phe Lys Pro Tyr Met Lys Gln His Leu Pro Lys Arg Leu
                420                 425                 430

His Tyr Ala Asn Asn Arg Arg Ile Glu Asp Leu His Leu Leu Val Glu
            435                 440                 445

Arg Arg Trp His Val Ala Arg Lys Pro Leu Asp Val Tyr Lys Lys Pro
    450                 455                 460

Ser Gly Lys Cys Phe Phe Gln Gly Asp His Gly Phe Asp Asn Lys Val
465                 470                 475                 480

Asn Ser Met Gln Thr Val Phe Val Gly Tyr Gly Pro Thr Phe Lys Tyr
                485                 490                 495

Arg Thr Lys Val Pro Pro Phe Glu Asn Ile Glu Leu Tyr Asn Val Met
                500                 505                 510

Cys Asp Leu Leu Ser Leu Lys Pro Ala Pro Asn Asn Gly Thr His Gly
            515                 520                 525

Ser Leu Asn His Leu Leu Arg Thr Asn Thr Phe Arg Pro Thr Leu Pro
    530                 535                 540

Glu Glu Val Ser Arg Thr Asn Tyr Pro Gly Ile Met Tyr Leu Gln Ser
545                 550                 555                 560

Asp Phe Asp Leu Gly Cys Thr Cys Asp Asp Lys Val Lys Pro Lys Asn
                565                 570                 575

Lys Leu Glu Glu Leu Asn Lys Arg Leu His Thr Lys Gly Ser Thr Glu
                580                 585                 590

Glu Arg His Leu Leu Tyr Gly Arg Pro Ala Val Leu Tyr Arg Thr Ser
            595                 600                 605

Tyr Asp Ile Leu Tyr His Thr Asp Phe Glu Ser Gly Tyr Ser Glu Ile
    610                 615                 620

Phe Leu Met Pro Leu Trp Thr Ser Tyr Thr Ile Ser Lys Gln Ala Glu
625                 630                 635                 640

Val Ser Ser Ile Pro Glu His Leu Thr Asn Cys Val Arg Pro Asp Val
                645                 650                 655

Arg Val Ser Pro Gly Phe Ser Gln Asn Cys Leu Ala Tyr Lys Asn Asp
                660                 665                 670

Lys Gln Met Ser Tyr Gly Phe Leu Phe Pro Pro Tyr Leu Ser Ser Ser
            675                 680                 685
```

```
Pro Glu Ala Lys Tyr Asp Ala Phe Leu Val Thr Asn Met Val Pro Met
    690                 695                 700
Tyr Pro Ala Phe Lys Arg Val Trp Thr Tyr Phe Gln Arg Val Leu Val
705                 710                 715                 720
Lys Lys Tyr Ala Ser Glu Arg Asn Gly Val Asn Val Ile Ser Gly Pro
                725                 730                 735
Ile Phe Asp Tyr Asn Tyr Asn Gly Leu Arg Asp Ile Glu Asp Glu Ile
            740                 745                 750
Lys Gln Tyr Val Glu Gly Ser Ser Ile Pro Val Pro Thr His Tyr Tyr
        755                 760                 765
Ser Ile Ile Thr Ser Cys Leu Asp Phe Thr Gln Pro Ala Asp Lys Cys
770                 775                 780
Asp Gly Pro Leu Ser Val Ser Ser Phe Ile Leu Pro His Arg Pro Asp
785                 790                 795                 800
Asn Asp Glu Ser Cys Asn Ser Ser Glu Asp Glu Ser Lys Trp Val Glu
                805                 810                 815
Glu Leu Met Lys Met His Thr Ala Arg Val Arg Asp Ile Glu His Leu
            820                 825                 830
Thr Gly Leu Asp Phe Tyr Arg Lys Thr Ser Arg Ser Tyr Ser Glu Ile
            835                 840                 845
Leu Thr Leu Lys Thr Tyr Leu His Thr Tyr Glu Ser Glu Ile
    850                 855                 860

<210> SEQ ID NO 13
<211> LENGTH: 20
<212> TYPE: DNA
<213> ORGANISM: Artificial Sequence
<220> FEATURE:
<223> OTHER INFORMATION: antisense DNA

<400> SEQUENCE: 13
gtcttgccat gccgagggat                                              20

<210> SEQ ID NO 14
<211> LENGTH: 20
<212> TYPE: DNA
<213> ORGANISM: Artificial Sequence
<220> FEATURE:
<223> OTHER INFORMATION: missense DNA

<400> SEQUENCE: 14
gttctcgcag tcgcaggagt                                              20
```